(12) United States Patent
Fritz et al.

(10) Patent No.: US 9,809,414 B2
(45) Date of Patent: Nov. 7, 2017

(54) ELASTIC BREAK BRAKE APPARATUS AND METHOD FOR MINIMIZING BROKEN ELASTIC RETHREADING

(71) Applicant: Curt G. Joa, Inc., Sheboygan Falls, WI (US)

(72) Inventors: Jeff W Fritz, Plymouth, WI (US); Chris Nelson, Plymouth, WI (US); John A McCabe, Sheboygan Falls, WI (US); Daniel A Peterson, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 878 days.

(21) Appl. No.: 13/868,712

(22) Filed: Apr. 23, 2013

(65) Prior Publication Data

US 2013/0277154 A1 Oct. 24, 2013

Related U.S. Application Data

(60) Provisional application No. 61/645,867, filed on May 11, 2012, provisional application No. 61/637,365, filed on Apr. 24, 2012.

(51) Int. Cl.
*B65H 63/024* (2006.01)
*B65H 57/14* (2006.01)
(Continued)

(52) U.S. Cl.
CPC ....... *B65H 57/14* (2013.01); *A61F 13/15804* (2013.01); *B65H 63/024* (2013.01);
(Continued)

(58) Field of Classification Search
CPC ....... B65H 63/02; B65H 63/024; B65H 57/14
(Continued)

(56) References Cited

U.S. PATENT DOCUMENTS 135,145 A 1/1873 Murphy
293,353 A 2/1884 Purvis
(Continued)

FOREIGN PATENT DOCUMENTS

BE 1007854 11/1995
CA 1146129 5/1983
(Continued)

OTHER PUBLICATIONS

International Search Report dated Jun. 19, 2013 regarding EP Application No. 13165203.4, 5 pages.
(Continued)

*Primary Examiner* — Michael C McCullough
(74) *Attorney, Agent, or Firm* — Ryan Kromholz & Manion, S.C.

(57) ABSTRACT

A series of elastic break brakes are provided throughout a travel path of elastics in a machine operation. Elastic strands thread through each individual brake mechanism, and if an elastic strand breaks downstream, a natural snap back of the elastic, which ordinarily travels through the system under tension, drives an immediately upstream cam mechanism back, and holds the elastic thread in place at the elastic break brake immediately upstream of the break as to minimize rethreading required downstream of the elastic break brake.

1 Claim, 16 Drawing Sheets

(51) Int. Cl.
*A61F 13/15* (2006.01)
*A61F 13/49* (2006.01)

(52) U.S. Cl.
CPC ... *A61F 13/15593* (2013.01); *A61F 13/15601* (2013.01); *A61F 13/49017* (2013.01); *A61F 13/49019* (2013.01)

(58) Field of Classification Search
USPC .................................................... 226/196.1
See application file for complete search history.

(56) References Cited

U.S. PATENT DOCUMENTS

| | | | |
|---|---|---|---|
| 312,257 A | 2/1885 | Cotton et al. |
| 410,123 A | 8/1889 | Sitwell |
| 432,742 A | 7/1890 | Stanley |
| 643,821 A | 2/1900 | Howlett |
| 1,393,524 A | 10/1921 | Grupe |
| 1,431,315 A | 10/1922 | Le Moine |
| 1,605,842 A | 11/1926 | Jones |
| 1,686,595 A | 10/1928 | Belluche |
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |
| 2,131,808 A | 10/1938 | Joa |
| 2,164,408 A | 7/1939 | Joa |
| 2,167,179 A | 7/1939 | Joa |
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,627,859 A | 2/1953 | Hargrave |
| 2,695,025 A | 11/1954 | Andrews |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,788,786 A | 4/1957 | Dexter |
| 2,811,905 A | 11/1957 | Kennedy, Jr. |
| 2,828,745 A | 4/1958 | Deutz |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,890,700 A | 6/1959 | Lonberg-Holm |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | De Neui et al. |
| 2,991,739 A | 7/1961 | Joa |
| 3,016,207 A | 1/1962 | Comstock, III |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,075,684 A | 1/1963 | Rothmann |
| 3,086,253 A | 4/1963 | Joa |
| 3,087,689 A | 4/1963 | Heim |
| 3,089,494 A | 5/1963 | Schwartz |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,318,608 A | 5/1967 | Smrekar |
| 3,322,589 A | 5/1967 | Joa |
| 3,342,184 A | 9/1967 | Joa |
| 3,356,092 A | 12/1967 | Joa |
| 3,360,103 A | 12/1967 | Joa |
| 3,336,847 A | 1/1968 | Johnson |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,527,123 A | 9/1970 | Dovey |
| 3,538,551 A | 11/1970 | Joa |
| 3,540,641 A | 11/1970 | Besnyo |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger et al. |
| 3,728,191 A | 4/1973 | Wierzba et al. |
| 3,751,224 A | 8/1973 | Wackerle |
| 3,758,102 A | 9/1973 | Munn et al. |
| 3,762,542 A | 10/1973 | Grimes |
| 3,772,120 A | 11/1973 | Radzins |
| 3,776,798 A | 12/1973 | Milano |
| 3,796,360 A | 3/1974 | Alexeff |
| 3,811,987 A | 5/1974 | Wilkinson et al. |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Gellert et al. |
| 3,903,768 A | 9/1975 | Amberg et al. |
| 3,904,147 A | 9/1975 | Taitel et al. |
| 3,918,698 A | 11/1975 | Coast |
| 3,921,481 A | 11/1975 | Fleetwood |
| 3,929,297 A * | 12/1975 | Zumfeld ............... B65H 63/028 242/419.4 |
| 3,941,038 A | 3/1976 | Bishop |
| 3,960,646 A | 6/1976 | Wiedamann |
| 3,988,194 A | 10/1976 | Babcock et al. |
| 3,991,994 A | 11/1976 | Farish |
| 4,002,005 A | 1/1977 | Mueller et al. |
| 4,003,298 A | 1/1977 | Schott, Jr. |
| 4,009,626 A | 3/1977 | Gressman |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |

(56) References Cited

U.S. PATENT DOCUMENTS

| | | |
|---|---|---|
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,220,237 A | 9/1980 | Mohn |
| 4,222,533 A | 9/1980 | Pongracz |
| 4,223,822 A | 9/1980 | Clitheroe |
| 4,231,129 A | 11/1980 | Winch |
| 4,234,157 A | 11/1980 | Hodgeman et al. |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,349,140 A | 9/1982 | Passafiume |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,426,897 A | 1/1984 | Littleton |
| 4,452,597 A | 6/1984 | Achelpohl |
| 4,479,836 A | 10/1984 | Dickover et al. |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,543,152 A | 9/1985 | Nozaka |
| 4,551,191 A | 11/1985 | Kock et al. |
| 4,578,133 A | 3/1986 | Oshefsky et al. |
| 4,586,199 A | 5/1986 | Birring |
| 4,589,945 A | 5/1986 | Polit |
| 4,603,800 A | 8/1986 | Focke et al. |
| 4,606,964 A | 8/1986 | Wideman |
| 4,608,115 A | 8/1986 | Schroth et al. |
| 4,610,681 A | 9/1986 | Strohbeen et al. |
| 4,610,682 A | 9/1986 | Kopp |
| 4,614,076 A | 9/1986 | Rathemacher |
| 4,619,357 A | 10/1986 | Radzins et al. |
| 4,625,612 A | 12/1986 | Oliver |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |
| 4,663,220 A | 5/1987 | Wisneski et al. |
| 4,672,705 A | 6/1987 | Bors et al. |
| 4,675,016 A | 6/1987 | Meuli et al. |
| 4,675,062 A | 6/1987 | Instance |
| 4,675,068 A | 6/1987 | Lundmark |
| 4,686,136 A | 8/1987 | Homonoff et al. |
| 4,693,056 A | 9/1987 | Raszewski |
| 4,701,239 A | 10/1987 | Craig |
| 4,720,415 A | 1/1988 | Vander Wielen et al. |
| 4,723,698 A | 2/1988 | Schoonderbeek |
| 4,726,874 A | 2/1988 | Van Vliet |
| 4,726,876 A | 2/1988 | Tomsovic, Jr. |
| 4,743,241 A | 5/1988 | Igaue et al. |
| 4,751,997 A | 6/1988 | Hirsch |
| 4,753,429 A | 6/1988 | Irvine et al. |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,451 A | 1/1989 | Buckley |
| 4,795,510 A | 1/1989 | Wittrock et al. |
| 4,798,353 A | 1/1989 | Peugh |
| 4,801,345 A | 1/1989 | Dussaud et al. |
| 4,802,570 A | 2/1989 | Hirsch et al. |
| 4,826,499 A | 5/1989 | Ahr |
| 4,840,609 A | 6/1989 | Jones et al. |
| 4,845,964 A | 7/1989 | Bors et al. |
| 4,864,802 A | 9/1989 | D'Angelo |
| 4,880,102 A | 11/1989 | Indrebo |
| 4,888,231 A | 12/1989 | Angstadt |
| 4,892,536 A | 1/1990 | Des Marais et al. |
| 4,904,440 A | 2/1990 | Angstadt |
| 4,908,175 A | 3/1990 | Angstadt |
| 4,909,019 A | 3/1990 | Delacretaz et al. |
| 4,915,767 A | 4/1990 | Rajala et al. |
| 4,917,746 A | 4/1990 | Kons |
| 4,925,520 A | 5/1990 | Beaudoin et al. |
| 4,927,322 A | 5/1990 | Schweizer et al. |
| 4,927,486 A | 5/1990 | Fattal et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,029,505 A | 7/1991 | Holiday |
| 5,045,039 A | 9/1991 | Bay |
| 5,045,135 A | 9/1991 | Meissner et al. |
| 5,062,597 A | 11/1991 | Martin et al. |
| 5,064,179 A | 11/1991 | Martin |
| 5,064,492 A | 11/1991 | Friesch |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski, Jr. et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,131,901 A | 7/1992 | Moll |
| 5,133,511 A | 7/1992 | Mack |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,190,234 A | 3/1993 | Ezekiel |
| 5,195,684 A | 3/1993 | Radzins |
| 5,203,043 A | 4/1993 | Riedel |
| 5,213,645 A | 5/1993 | Nomura et al. |
| 5,222,422 A | 6/1993 | Benner, Jr. et al. |
| 5,223,069 A | 6/1993 | Tokuno et al. |
| 5,226,992 A | 7/1993 | Morman |
| 5,246,433 A | 9/1993 | Hasse et al. |
| 5,252,228 A | 10/1993 | Stokes |
| 5,267,933 A | 12/1993 | Precoma |
| 5,273,228 A | 12/1993 | Yoshida |
| 5,275,076 A | 1/1994 | Greenwalt |
| 5,275,676 A | 1/1994 | Rooyakkers et al. |
| 5,308,345 A | 5/1994 | Herrin |
| 5,328,438 A | 7/1994 | Crowley |
| 5,334,446 A | 8/1994 | Quantrille et al. |
| 5,340,424 A | 8/1994 | Matsushita |
| 5,353,909 A | 10/1994 | Mukai |
| 5,368,893 A | 11/1994 | Sommer et al. |
| 5,389,173 A | 2/1995 | Merkatoris et al. |
| 5,393,360 A | 2/1995 | Bridges et al. |
| 5,407,507 A | 4/1995 | Ball |
| 5,407,513 A | 4/1995 | Hayden et al. |
| 5,410,857 A | 5/1995 | Utley |
| 5,415,649 A | 5/1995 | Watanabe et al. |
| 5,417,132 A | 5/1995 | Cox et al. |
| 5,421,924 A | 6/1995 | Ziegelhoffer et al. |
| 5,424,025 A | 6/1995 | Hanschen et al. |

(56) References Cited

U.S. PATENT DOCUMENTS

| | | |
|---|---|---|
| 5,429,576 A | 7/1995 | Doderer-Winkler |
| 5,435,802 A | 7/1995 | Kober |
| 5,435,971 A | 7/1995 | Dyckman |
| 5,449,353 A | 9/1995 | Watanabe et al. |
| 5,464,401 A | 11/1995 | Hasse et al. |
| 5,486,253 A | 1/1996 | Otruba |
| 5,494,622 A | 2/1996 | Heath et al. |
| 5,500,075 A | 3/1996 | Herrmann |
| 5,516,392 A | 5/1996 | Bridges et al. |
| 5,518,566 A | 5/1996 | Bridges et al. |
| 5,525,175 A | 6/1996 | Blenke et al. |
| 5,531,850 A | 7/1996 | Herrmann |
| 5,540,647 A | 7/1996 | Weiermann et al. |
| 5,540,796 A | 7/1996 | Fries |
| 5,545,275 A | 8/1996 | Herrin et al. |
| 5,545,285 A | 8/1996 | Johnson |
| 5,552,013 A | 9/1996 | Ehlert et al. |
| 5,555,786 A | 9/1996 | Fuller |
| 5,556,360 A | 9/1996 | Kober et al. |
| 5,556,504 A | 9/1996 | Rajala et al. |
| 5,560,793 A | 10/1996 | Ruscher et al. |
| 5,575,187 A | 11/1996 | Dieterlen |
| 5,586,964 A | 12/1996 | Chase |
| 5,602,747 A | 2/1997 | Rajala |
| 5,603,794 A | 2/1997 | Thomas |
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,636,500 A | 6/1997 | Gould |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| 5,683,531 A | 11/1997 | Roessler et al. |
| 5,685,873 A | 11/1997 | Bruemmer |
| RE35,687 E | 12/1997 | Igaue et al. |
| 5,693,165 A | 12/1997 | Schmitz |
| 5,699,653 A | 12/1997 | Hartman et al. |
| 5,705,013 A | 1/1998 | Nease |
| 5,707,470 A | 1/1998 | Rajala et al. |
| 5,711,832 A | 1/1998 | Glaug et al. |
| 5,725,518 A | 3/1998 | Coates |
| 5,725,714 A | 3/1998 | Fujioka |
| 5,743,994 A | 4/1998 | Roessler et al. |
| 5,745,922 A | 5/1998 | Rajala et al. |
| 5,746,869 A | 5/1998 | Hayden et al. |
| 5,749,989 A | 5/1998 | Linman et al. |
| 5,759,340 A | 6/1998 | Boothe et al. |
| 5,766,389 A | 6/1998 | Brandon et al. |
| 5,766,411 A | 6/1998 | Wilson |
| 5,779,689 A | 7/1998 | Pfeifer et al. |
| 5,788,797 A | 8/1998 | Herrin et al. |
| 5,817,199 A | 10/1998 | Brennecke et al. |
| 5,827,259 A | 10/1998 | Laux et al. |
| 5,829,164 A | 11/1998 | Kotischke |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,876,792 A | 3/1999 | Caldwell |
| 5,879,500 A | 3/1999 | Herrin et al. |
| 5,902,431 A | 5/1999 | Wilkinson et al. |
| 5,904,675 A | 5/1999 | Laux et al. |
| 5,932,039 A | 8/1999 | Popp et al. |
| 5,935,367 A | 8/1999 | Hollenbeck |
| 5,938,193 A | 8/1999 | Bluemle et al. |
| 5,938,652 A | 8/1999 | Sauer |
| 5,964,390 A | 10/1999 | Borresen et al. |
| 5,964,970 A | 10/1999 | Woolwine et al. |
| 5,971,134 A | 10/1999 | Trefz et al. |
| 5,983,764 A | 11/1999 | Hillebrand |
| 6,009,781 A | 1/2000 | McNeil |
| 6,022,443 A | 2/2000 | Rajala et al. |
| 6,036,805 A | 3/2000 | McNichols |
| 6,043,836 A | 3/2000 | Kerr et al. |
| 6,050,517 A | 4/2000 | Dobrescu et al. |
| 6,074,110 A | 6/2000 | Verlinden et al. |
| 6,076,442 A | 6/2000 | Arterburn et al. |
| 6,080,909 A | 6/2000 | Osterdahl et al. |
| 6,098,249 A | 8/2000 | Toney et al. |
| 6,123,792 A | 9/2000 | Samida et al. |
| 6,142,048 A | 11/2000 | Bradatsch et al. |
| 6,171,432 B1 | 1/2001 | Brisebois |
| 6,183,576 B1 | 2/2001 | Couillard et al. |
| 6,193,054 B1 | 2/2001 | Henson et al. |
| 6,193,702 B1 | 2/2001 | Spencer |
| 6,195,850 B1 | 3/2001 | Melbye |
| 6,210,386 B1 | 4/2001 | Inoue |
| 6,212,859 B1 | 4/2001 | Bielik, Jr. et al. |
| 6,214,147 B1 | 4/2001 | Mortellite et al. |
| 6,250,048 B1 | 6/2001 | Linkiewicz |
| 6,264,639 B1 | 7/2001 | Sauer |
| 6,264,784 B1 | 7/2001 | Menard et al. |
| 6,276,421 B1 | 8/2001 | Valenti et al. |
| 6,276,587 B1 | 8/2001 | Borresen |
| 6,280,373 B1 | 8/2001 | Lanvin |
| 6,284,081 B1 | 9/2001 | Vogt et al. |
| 6,287,409 B1 | 9/2001 | Stephany |
| 6,305,260 B1 | 10/2001 | Truttmann et al. |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,319,347 B1 | 11/2001 | Rajala |
| 6,336,921 B1 | 1/2002 | Kato et al. |
| 6,336,922 B1 | 1/2002 | VanGompel et al. |
| 6,336,923 B1 | 1/2002 | Fujioka et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,431,038 B2 | 8/2002 | Couturier |
| 6,440,246 B1 | 8/2002 | Vogt et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Glaug et al. |
| 6,482,278 B1 | 11/2002 | McCabe et al. |
| 6,494,244 B2 | 12/2002 | Parrish et al. |
| 6,514,233 B1 | 2/2003 | Glaug |
| 6,521,320 B2 | 2/2003 | McCabe et al. |
| 6,523,595 B1 | 2/2003 | Milner et al. |
| 6,524,423 B1 | 2/2003 | Hilt et al. |
| 6,533,879 B2 | 3/2003 | Quereshi et al. |
| 6,540,857 B1 | 4/2003 | Coenen et al. |
| 6,547,909 B1 | 4/2003 | Butterworth |
| 6,550,517 B1 | 4/2003 | Hilt et al. |
| 6,551,228 B1 | 4/2003 | Richards |
| 6,551,430 B1 | 4/2003 | Glaug et al. |
| 6,554,815 B1 | 4/2003 | Umebayashi |
| 6,569,275 B1 | 5/2003 | Popp et al. |
| 6,572,520 B2 | 6/2003 | Blumle |
| 6,581,517 B1 | 6/2003 | Becker et al. |
| 6,585,841 B1 | 7/2003 | Popp et al. |
| 6,589,149 B1 | 7/2003 | VanEperen et al. |
| 6,596,107 B2 | 7/2003 | Stopher |
| 6,596,108 B2 | 7/2003 | McCabe |
| 6,605,172 B1 | 8/2003 | Anderson et al. |
| 6,605,173 B1 | 8/2003 | Glaug et al. |
| 6,620,276 B1 | 9/2003 | Kuntze et al. |
| 6,634,269 B2 | 10/2003 | Eckstein et al. |
| 6,637,583 B1 | 10/2003 | Andersson |
| 6,648,122 B1 | 11/2003 | Hirsch et al. |
| 6,649,010 B2 | 11/2003 | Parrish et al. |
| 6,656,309 B1 | 12/2003 | Parker et al. |
| 6,659,150 B1 | 12/2003 | Perkins et al. |

(56) References Cited

U.S. PATENT DOCUMENTS

| | | |
|---|---|---|
| 6,659,991 B2 | 12/2003 | Suckane |
| 6,675,552 B2 | 1/2004 | Kunz et al. |
| 6,682,626 B2 | 1/2004 | Mlinar et al. |
| 6,684,925 B2 | 2/2004 | Nagate et al. |
| 6,722,494 B2 | 4/2004 | Nakakado |
| 6,730,189 B1 | 5/2004 | Franzmann |
| 6,743,324 B2 | 6/2004 | Hargett et al. |
| 6,750,407 B2 | 6/2004 | Song |
| 6,758,109 B2 | 7/2004 | Nakakado |
| 6,766,817 B2 | 7/2004 | da Silva |
| 6,779,426 B1 | 8/2004 | Holliday |
| 6,808,582 B2 | 10/2004 | Popp et al. |
| D497,991 S | 11/2004 | Otsubo et al. |
| 6,811,019 B2 | 11/2004 | Christian et al. |
| 6,811,642 B2 | 11/2004 | Ochi |
| 6,814,217 B2 | 11/2004 | Blumenthal et al. |
| 6,820,671 B2 | 11/2004 | Calvert |
| 6,837,840 B2 | 1/2005 | Yonekawa et al. |
| 6,840,616 B2 | 1/2005 | Summers |
| 6,852,186 B1 | 2/2005 | Matsuda et al. |
| 6,869,494 B2 | 3/2005 | Roessler et al. |
| 6,875,202 B2 | 4/2005 | Kumasaka et al. |
| 6,884,310 B2 | 4/2005 | Roessler et al. |
| 6,893,528 B2 | 5/2005 | Middelstadt et al. |
| 6,913,718 B2 | 7/2005 | Ducker |
| 6,918,404 B2 | 7/2005 | Dias da Silva |
| 6,976,521 B2 | 12/2005 | Mlinar |
| 6,978,486 B2 | 12/2005 | Zhou et al. |
| 7,017,321 B2 | 3/2006 | Salvoni |
| 7,017,820 B1 | 3/2006 | Brunner |
| 7,045,031 B2 | 5/2006 | Popp et al. |
| 7,047,852 B2 | 5/2006 | Franklin et al. |
| 7,048,725 B2 | 5/2006 | Kling et al. |
| 7,066,586 B2 | 6/2006 | da Silva |
| 7,069,970 B2 | 7/2006 | Tomsovic et al. |
| 7,077,393 B2 | 7/2006 | Ishida |
| 7,130,710 B2 | 10/2006 | Popp et al. |
| 7,137,971 B2 | 11/2006 | Tanzer |
| 7,172,666 B2 | 2/2007 | Groves et al. |
| 7,175,584 B2 | 2/2007 | Maxton et al. |
| 7,195,684 B2 | 3/2007 | Satoh |
| 7,201,345 B2 | 4/2007 | Werner |
| 7,214,174 B2 | 5/2007 | Allen et al. |
| 7,214,287 B2 | 5/2007 | Shiomi |
| 7,220,335 B2 | 5/2007 | Van Gompel et al. |
| 7,247,219 B2 | 7/2007 | O'Dowd |
| 7,252,730 B2 | 8/2007 | Hoffman et al. |
| 7,264,686 B2 | 9/2007 | Thorson et al. |
| 7,303,708 B2 | 12/2007 | Andrews et al. |
| 7,326,311 B2 | 2/2008 | Krueger et al. |
| 7,332,459 B2 | 2/2008 | Collins et al. |
| 7,374,627 B2 | 5/2008 | McCabe |
| 7,380,213 B2 | 5/2008 | Pokorny et al. |
| 7,398,870 B2 | 7/2008 | McCabe |
| 7,449,084 B2 | 11/2008 | Nakakado |
| 7,452,436 B2 | 11/2008 | Andrews |
| 7,533,709 B2 | 5/2009 | Meyer |
| 7,537,215 B2 | 5/2009 | Beaudoin et al. |
| 7,587,966 B2 | 9/2009 | Nakakado et al. |
| 7,618,513 B2 | 11/2009 | Meyer |
| 7,638,014 B2 | 12/2009 | Coose et al. |
| 7,640,962 B2 | 1/2010 | Meyer et al. |
| 7,695,464 B2 | 4/2010 | Fletcher et al. |
| 7,703,599 B2 | 4/2010 | Meyer |
| 7,708,849 B2 | 5/2010 | McCabe |
| 7,770,712 B2 | 8/2010 | McCabe |
| 7,771,407 B2 | 8/2010 | Umebayashi |
| 7,780,052 B2 | 8/2010 | McCabe |
| 7,793,772 B2 | 9/2010 | Schafer |
| 7,811,403 B2 | 10/2010 | Andrews |
| 7,861,756 B2 | 1/2011 | Jenquin et al. |
| 7,871,400 B2 | 1/2011 | Sablone et al. |
| 7,909,956 B2 | 3/2011 | Coose et al. |
| 7,922,983 B2 | 4/2011 | Prokash et al. |
| 7,935,296 B2 | 5/2011 | Koele et al. |
| 7,975,584 B2 | 7/2011 | McCabe |
| 7,987,964 B2 | 8/2011 | McCabe |
| 8,007,484 B2 | 8/2011 | McCabe et al. |
| 8,007,623 B2 | 8/2011 | Andrews |
| 8,011,493 B2 | 9/2011 | Giuliani et al. |
| 8,016,972 B2 | 9/2011 | Andrews et al. |
| 8,025,652 B2 | 9/2011 | Hornung et al. |
| 8,062,459 B2 | 11/2011 | Nakakado et al. |
| 8,100,173 B2 | 1/2012 | Hornung et al. |
| 8,172,977 B2 | 5/2012 | Andrews et al. |
| 8,176,573 B2 | 5/2012 | Popp et al. |
| 8,178,035 B2 | 5/2012 | Edvardsson et al. |
| 8,182,624 B2 | 5/2012 | Handziak |
| 8,182,735 B2 | 5/2012 | Edvardsson |
| 8,182,736 B2 | 5/2012 | Edvardsson |
| 8,293,056 B2 | 10/2012 | McCabe |
| 8,381,489 B2 | 2/2013 | Freshwater et al. |
| 8,398,793 B2 | 3/2013 | Andrews et al. |
| 8,417,374 B2 | 4/2013 | Meyer et al. |
| 8,460,495 B2 | 6/2013 | McCabe |
| 8,512,496 B2 | 8/2013 | Makimura |
| 2001/0012813 A1 | 8/2001 | Bluemle |
| 2001/0017181 A1 | 8/2001 | Otruba et al. |
| 2001/0035332 A1 | 11/2001 | Zeitler |
| 2001/0042591 A1 | 11/2001 | Milner et al. |
| 2002/0040630 A1 | 4/2002 | Piazza |
| 2002/0046802 A1 | 4/2002 | Tachibana et al. |
| 2002/0059013 A1 | 5/2002 | Rajala et al. |
| 2002/0096241 A1 | 7/2002 | Instance |
| 2002/0125105 A1 | 9/2002 | Nakakado |
| 2002/0162776 A1 | 11/2002 | Hergeth |
| 2003/0000620 A1 | 1/2003 | Herrin et al. |
| 2003/0015209 A1 | 1/2003 | Gingras et al. |
| 2003/0051802 A1 | 3/2003 | Hargett et al. |
| 2003/0052148 A1 | 3/2003 | Rajala et al. |
| 2003/0066585 A1 | 4/2003 | McCabe |
| 2003/0083638 A1 | 5/2003 | Molee |
| 2003/0084984 A1 | 5/2003 | Glaug et al. |
| 2003/0089447 A1 | 5/2003 | Molee et al. |
| 2003/0115660 A1 | 6/2003 | Hopkins |
| 2003/0121244 A1 | 7/2003 | Abba |
| 2003/0121614 A1 | 7/2003 | Tabor et al. |
| 2003/0135189 A1 | 7/2003 | Umebayashi |
| 2003/0150551 A1 | 8/2003 | Baker |
| 2004/0007328 A1 | 1/2004 | Popp et al. |
| 2004/0016500 A1 | 1/2004 | Tachibana et al. |
| 2004/0044325 A1 | 3/2004 | Corneliusson |
| 2004/0073187 A1 | 4/2004 | Karami |
| 2004/0087425 A1 | 5/2004 | Ng et al. |
| 2004/0098791 A1 | 5/2004 | Faulks |
| 2004/0112517 A1 | 6/2004 | Groves et al. |
| 2004/0164482 A1 | 8/2004 | Edinger |
| 2004/0167493 A1 | 8/2004 | Jarpenberg et al. |
| 2004/0177737 A1 | 9/2004 | Adami |
| 2004/0182213 A1 | 9/2004 | Wagner et al. |
| 2004/0182497 A1 | 9/2004 | Lowrey |
| 2004/0216830 A1 | 11/2004 | Van Eperen |
| 2005/0000628 A1 | 1/2005 | Norrby |
| 2005/0022476 A1 | 2/2005 | Hamer |
| 2005/0056678 A1 | 3/2005 | Nomura et al. |
| 2005/0077418 A1 | 4/2005 | Werner et al. |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0011030 A1 | 1/2006 | Wagner et al. |
| 2006/0021300 A1 | 2/2006 | Tada et al. |
| 2006/0137298 A1 | 6/2006 | Oshita et al. |
| 2006/0201619 A1 | 9/2006 | Andrews |
| 2006/0224137 A1 | 10/2006 | McCabe et al. |
| 2006/0265867 A1 | 11/2006 | Schaap |
| 2007/0074953 A1 | 4/2007 | McCabe |
| 2007/0131343 A1 | 6/2007 | Nordang |
| 2007/0131817 A1 | 6/2007 | Fromm |
| 2008/0041206 A1 | 2/2008 | Mergola et al. |
| 2008/0210067 A1 | 9/2008 | Schlinz et al. |

(56) References Cited

U.S. PATENT DOCUMENTS

| | | |
|---|---|---|
| 2008/0223537 A1 | 9/2008 | Wiedmann |
| 2008/0281286 A1 | 11/2008 | Peterson |
| 2008/0287898 A1 | 11/2008 | Guzman Reyes |
| 2009/0020211 A1 | 1/2009 | Andrews et al. |
| 2009/0126864 A1 | 5/2009 | Tachibana et al. |
| 2009/0198205 A1 | 8/2009 | Malowaniec et al. |
| 2009/0212468 A1 | 8/2009 | Edvardsson et al. |
| 2010/0078119 A1 | 4/2010 | Yamamoto |
| 2010/0078120 A1 | 4/2010 | Otsubo |
| 2010/0078127 A1 | 4/2010 | Yamamoto |
| 2010/0193135 A1 | 8/2010 | Eckstein et al. |
| 2010/0193138 A1 | 8/2010 | Eckstein |
| 2010/0193155 A1 | 8/2010 | Nakatani |
| 2010/0249737 A1 | 9/2010 | Ito et al. |
| 2011/0106042 A1 | 5/2011 | Sablone et al. |
| 2011/0144611 A1 | 6/2011 | Saito |
| 2012/0079926 A1 | 4/2012 | Long et al. |
| 2012/0123377 A1 | 5/2012 | Back |
| 2012/0270715 A1 | 10/2012 | Motegi et al. |
| 2012/0285306 A1 | 11/2012 | Weibelt |
| 2012/0310193 A1 | 12/2012 | Ostertag |
| 2012/0312463 A1 | 12/2012 | Ogasawara et al. |

FOREIGN PATENT DOCUMENTS

| | | |
|---|---|---|
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2330679 | 9/1999 |
| CA | 2404154 | 10/2001 |
| CA | 2541194 | 10/2006 |
| CA | 2559517 | 4/2007 |
| CA | 2337700 | 8/2008 |
| CA | 2407867 | 6/2010 |
| CA | 2699136 | 10/2010 |
| CA | 142627 | 6/2013 |
| CA | 2600432 | 7/2013 |
| CN | 202105105 | 1/2012 |
| DE | 60123502 | 10/2006 |
| DE | 60216550 | 12/2006 |
| DE | 102005035544 | 2/2007 |
| DE | 102005048868 | 4/2007 |
| DE | 102006047280 | 4/2007 |
| DE | 102007063209 | 6/2009 |
| DE | 102007063209 A1 | 6/2009 |
| EP | 0044206 | 1/1982 |
| EP | 0048011 | 3/1982 |
| EP | 0089106 | 9/1983 |
| EP | 0099732 | 2/1984 |
| EP | 0206208 | 12/1986 |
| EP | 0304140 | 2/1989 |
| EP | 0411287 | 2/1991 |
| EP | 0439897 | 8/1991 |
| EP | 0455231 A1 | 11/1991 |
| EP | 510251 | 10/1992 |
| EP | 0589859 | 3/1994 |
| EP | 0676352 | 4/1995 |
| EP | 0652175 A1 | 5/1995 |
| EP | 0811473 | 12/1997 |
| EP | 0901780 | 3/1999 |
| EP | 0990588 | 4/2000 |
| EP | 1132325 A2 | 9/2001 |
| EP | 1035818 | 4/2002 |
| EP | 1199057 | 4/2002 |
| EP | 1366734 | 12/2003 |
| EP | 1393701 | 3/2004 |
| EP | 1415628 | 5/2004 |
| EP | 1433731 | 6/2004 |
| EP | 1571249 | 9/2005 |
| EP | 1619008 | 1/2006 |
| EP | 1707168 A2 | 10/2006 |
| EP | 1726414 | 11/2006 |
| EP | 1302424 | 12/2006 |
| EP | 1801045 | 6/2007 |
| EP | 1941853 | 7/2008 |
| EP | 1961403 | 8/2008 |
| EP | 1994919 | 11/2008 |
| EP | 2180864 | 11/2008 |
| EP | 2211812 | 11/2008 |
| EP | 2103427 | 9/2009 |
| EP | 2233116 | 9/2010 |
| EP | 2238955 | 10/2010 |
| EP | 1175880 | 5/2012 |
| EP | 1868821 | 1/2013 |
| EP | 2036522 | 3/2013 |
| EP | 1272347 | 4/2013 |
| EP | 2032338 | 8/2013 |
| ES | 509706 | 11/1982 |
| ES | 520559 | 12/1983 |
| ES | 296211 | 12/1987 |
| ES | 200601373 | 7/2009 |
| ES | 2311349 | 9/2009 |
| FR | 2177355 | 11/1973 |
| FR | 2255961 | 7/1975 |
| FR | 1132325 | 10/2006 |
| FR | 2891811 | 4/2007 |
| GB | 191101501 A | 0/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 1467470 | 3/1977 |
| GB | 2045298 | 10/1980 |
| GB | 2115775 | 9/1983 |
| GB | 2288316 | 10/1995 |
| IT | 1374910 | 5/2010 |
| IT | 1374911 | 5/2010 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 A | 7/1994 |
| JP | 9299398 | 11/1997 |
| JP | 10035621 | 2/1998 |
| JP | 10-277091 A | 10/1998 |
| JP | 2008-161300 | 7/2008 |
| SE | 0602047 | 5/2007 |
| SE | 0601003-7 | 6/2007 |
| SE | 0601145-6 | 10/2009 |
| WO | WO93/15248 | 8/1993 |
| WO | WO9403301 | 2/1994 |
| WO | WO97/23398 | 7/1997 |
| WO | WO9732552 | 9/1997 |
| WO | WO9747265 | 12/1997 |
| WO | WO9747810 | 12/1997 |
| WO | WO9821134 | 5/1998 |
| WO | WO98/55298 | 12/1998 |
| WO | WO9907319 | 2/1999 |
| WO | WO9913813 A1 | 3/1999 |
| WO | WO9932385 | 7/1999 |
| WO | WO9965437 | 12/1999 |
| WO | WO0143682 | 6/2001 |
| WO | WO0172237 | 10/2001 |
| WO | WO0172237 A2 | 10/2001 |
| WO | WO03/031177 | 4/2003 |
| WO | WO2004007329 | 1/2004 |
| WO | WO2005075163 | 8/2005 |
| WO | WO2006038946 | 4/2006 |
| WO | WO2007029115 | 3/2007 |
| WO | WO2007039800 | 4/2007 |
| WO | WO2007126347 | 11/2007 |
| WO | WO2008001209 | 1/2008 |

(56) References Cited

FOREIGN PATENT DOCUMENTS

| WO | WO2008/015594 | 2/2008 |
| WO | WO2008037281 | 4/2008 |
| WO | WO2008/123348 | 10/2008 |
| WO | WO2008155618 | 12/2008 |
| WO | WO2009/065497 | 3/2009 |
| WO | WO2009/065500 | 3/2009 |
| WO | WO2010028786 | 3/2010 |
| WO | WO2011101773 | 8/2011 |

OTHER PUBLICATIONS

International Search Report dated Jun. 19, 2013 regarding EP Application No. 13165195.2, 4 pages.

\* cited by examiner

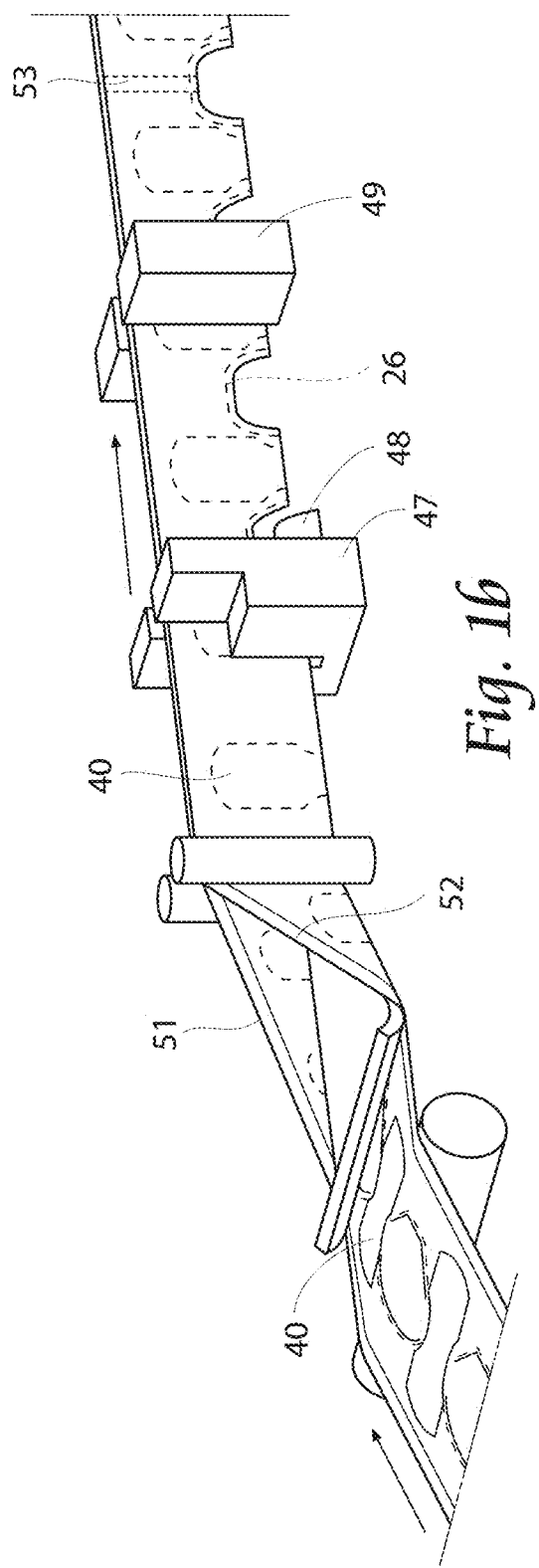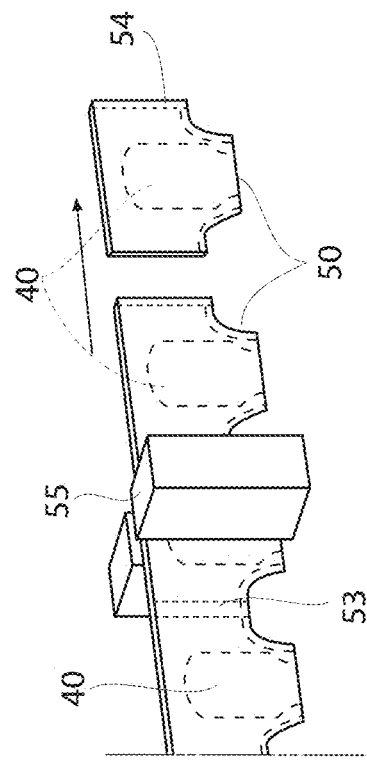

ELASTIC BREAK BRAKE APPARATUS AND METHOD FOR MINIMIZING BROKEN ELASTIC RETHREADING

RELATED APPLICATIONS

This application claims the benefit of provisional application Ser. Nos. 61/637,365 filed 24 Apr. 2012 and 61/645,867 filed 11 May 2012.

BACKGROUND OF THE INVENTION

The invention relates to disposable garments, and more particularly, a pants-type diaper, which is equipped with elastic strips effectively encircling the leg-holes without traversing the crotch region and to a method for producing such diapers.

Disposable diapers of the children's training pant type, or of the adult incontinence type, are typically equipped with elastic strands, which encircle the leg-holes. These strands of elastic are typically captured with adhesive between two layers of non-woven materials. Various methods are used to position these elastic strands so that they produce the desired encircling effect.

In one method of manufacture, the diapers are produced in an orientation whereby product flow is in the form of a single continuous web and the direction of travel is at a right angle with respect to what would be described as the crotch line of the diaper, i.e., the normal direction of product flow is parallel to the waist as opposed to parallel to the crotch.

One method of creating the desired effect of encircling the leg holes of the pant with elastics is to interleave two swaths of elastic strands, each curving across the face of the traveling web, encircling about one half of the leg-hole areas and crossing the path of the other. As a pair, they create a boundary around each leg-hole cutout, which resembles a circle or ellipse. In practice, however, the lateral excursions of the elastic lay-down device are speed-limited. As the traveling web is moving at some speed in one direction, and as the elastic lay-down device has speed and acceleration limits in the cross-direction, there is a limit to the steepness of the oblique angle which it is possible to form between the two. The result of this limitation is usually seen in the form of apparent incompleteness in the formation of the leg-hole-encircling pattern, particularly at the crotch line, where the two swaths cross each other.

From the point on the web at which one leg-hole pattern has been completed to the point at which the next can be begun, the elastic laydown device must reposition itself to a favorable starting point. This period of repositioning occurs as the crotch region passes the laydown device. As a result, the elastic strands must also cross this region of the product, at which they may or may not be attached by means of adhesives to the carrier webs. Various means are used to control or limit the positional relationships of the elastic strands in this region. The two sets of strands may cross over each other, creating an "X" pattern, or, they may loop back over to their respective sides, creating an "O" at the center of the crotch region. Alternatively, they may be mechanically stopped and prevented from crossing each other, creating two sets of generally parallel lines at the crotch The lay-down pattern used at the crotch will determine the final appearance of the product in this area.

The shirring effect created by elastic strands when laminated with any flexible fabric is well known. However, to have this shirring effect applied to the crotch of a pant-type garment can be undesirable. The elastics create a contractile force, which tends to distort the garment at this location, thereby reducing the garment's aesthetic appeal, effectiveness and comfort. Thus various methods of reducing or eliminating the effects of the elastic tension normally occurring at the crotch have been attempted. These methods include the elimination of the adhesive bond between the strands and the liner materials described in U.S. Pat. No. 5,745,922 as "unsecured space" as well as various methods of cutting the strands to eliminate their effects.

As mentioned, one method of eliminating the undesired effects of the elastic strands which cross the crotch region is to sever them. This method is described in U.S. Pat. No. 5,660,657. Unfortunately, such severing usually requires the introduction of a transversely extending cut, which can result in a loss of web tension in the severed part of the carrier web. This also creates an undesirable opening in the diaper backsheet. A proposed solution for this problem is taught in U.S. Pat. No. 5,707,470, wherein an ultrasonic device is used to sever the elastic members, while the carrier webs which encapsulate the elastics are left intact. See, also, U.S. Pat. No. 5,643,396. Another problem associated with such severing lies in the tendency of the unsecured severed ends of elastic to retract to some point beyond the limits of any adhesive pattern. Thus, the elastic strands are not controlled or anchored near the ends of the adhesion pattern and may snap back to further into the adhesive pattern. This results in an incomplete elastic pattern and poor product characteristics.

One method of compensating for the incompleteness of the encircling pattern entails insertion of an additional set of elastic strips, running parallel to the crotch line and transverse to the web path. See U.S. Pat. Nos. 5,634,917 and 5,660,657. Typical products of this type are provided with an outer laminate, which is formed of an inner liner material and an outer backsheet material, between which the leg-hole elastics are disposed.

Often, leg elastics or other types of continuous ribbons are applied to running webs in a sinusoidal pattern by a roll-fed web process. Roll-fed web processes typically use a constant infeed rate, which in the case of a sinusoidal ribbon application, can result in necking, or undesirable narrowing of the ribbon toward the inner and outer portions of the sine curve in the cross-machine direction. This is because the infeed rate of the ribbon web does not match with the velocity of the substrate it is being laid upon in the machine direction. Instead, the ribbon material is stretched somewhat at the extremities of the sine curve.

Roll-fed web processes typically use splicers and accumulators to assist in providing continuous webs during web processing operations. A first web is fed from a supply wheel (the expiring roll) into the manufacturing process. As the material from the expiring roll is depleted, it is necessary to splice the leading edge of a second web from a standby roll to the first web on the expiring roll in a manner that will not cause interruption of the web supply to a web consuming or utilizing device.

In a splicing system, a web accumulation dancer system may be employed, in which an accumulator collects a substantial length of the first web. By using an accumulator, the material being fed into the process can continue, yet the trailing end of the material can be stopped or slowed for a short time interval so that it can be spliced to leading edge of the new supply roll. The leading portion of the expiring roll remains supplied continuously to the web-utilizing device. The accumulator continues to feed the web utilization process while the expiring roll is stopped and the new web on a standby roll can be spliced to the end of the expiring roll.

In this manner, the device has a constant web supply being paid out from the accumulator, while the stopped web material in the accumulator can be spliced to the standby roll. Examples of web accumulators include that disclosed in U.S. patent application Ser. No. 11/110,616, which is commonly owned by the assignee of the present application, and incorporated herein by reference.

Examples of curved elastic application are disclosed in U.S. Pat. No. 6,482,278, incorporated herein by reference. Other examples include U.S. Pat. Nos. 8,100,173 and 8,025,652.

During the use of elastics in manufacturing disposable products, a continuous web of elastic is often threaded through numerous pieces of machinery upstream of a deposition point and adhesion of the elastic to another running web, such as a nonwoven material. If for some reason an elastic strand breaks during machine operation, it is necessary to re-thread the elastic through all of the machinery both upstream and downstream of the break.

SUMMARY OF THE INVENTION

Provided are methods and an apparatus for applying parallel flared elastics to a substrate used to form a disposable product, and severing elastics contained in a laminate from a leg hole opening. Other novel laydown patterns of elastics are also disclosed.

A series of elastic break brakes are provided throughout a travel path of elastics in a machine operation. Elastic strands thread through each individual brake mechanism, and if an elastic strand breaks downstream, a natural snap back of the elastic, which ordinarily travels through the system under tension, drives an immediately upstream cam mechanism back, and holds the elastic thread in place at the elastic break brake immediately upstream of the break as to minimize rethreading required downstream of the elastic break brake.

BRIEF DESCRIPTION OF THE DRAWINGS

FIGS. 1a-1c, collectively, are perspective views showing a preferred embodiment of the invention in somewhat diagrammatic fashion;

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1A:
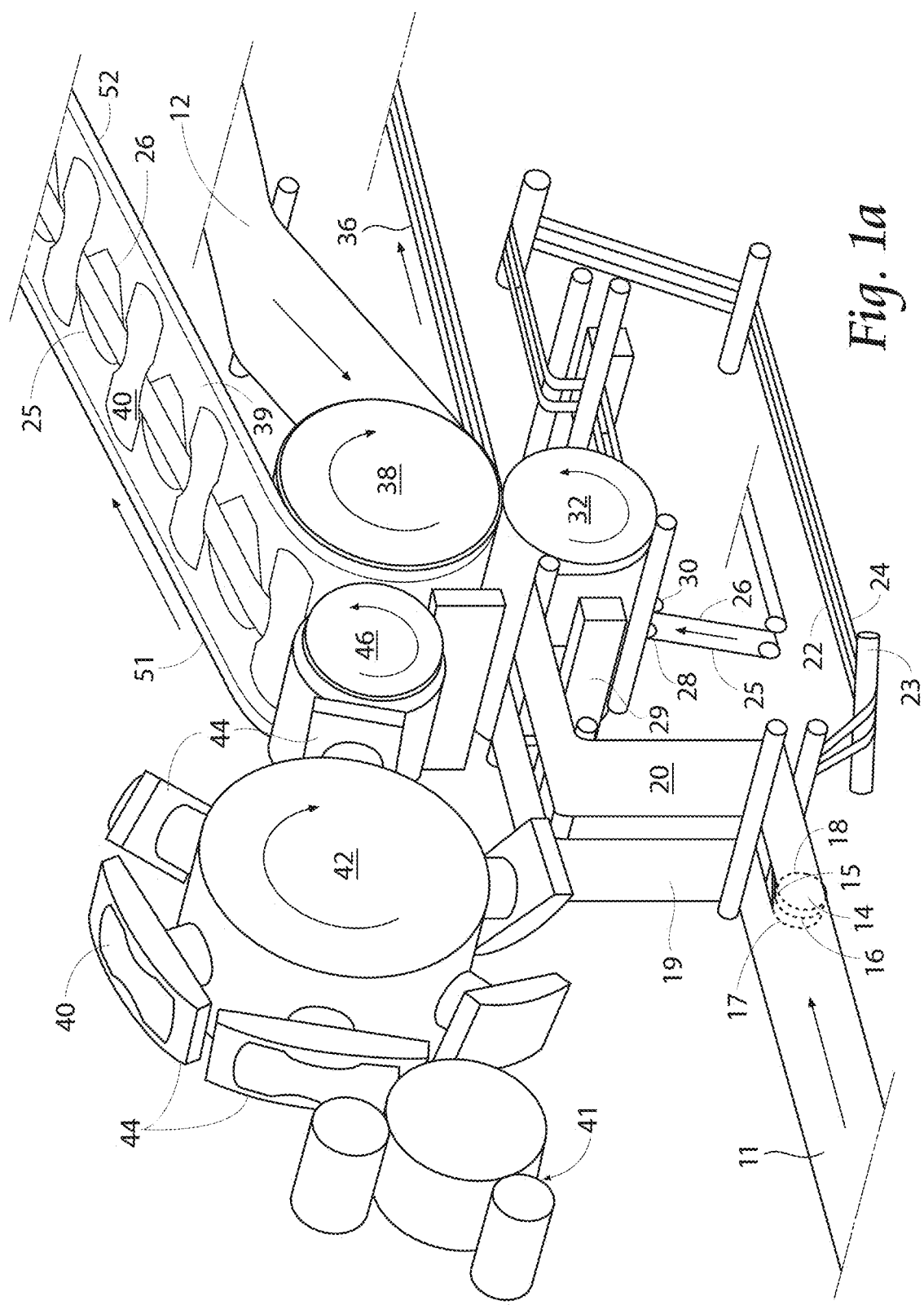
Figure 2:
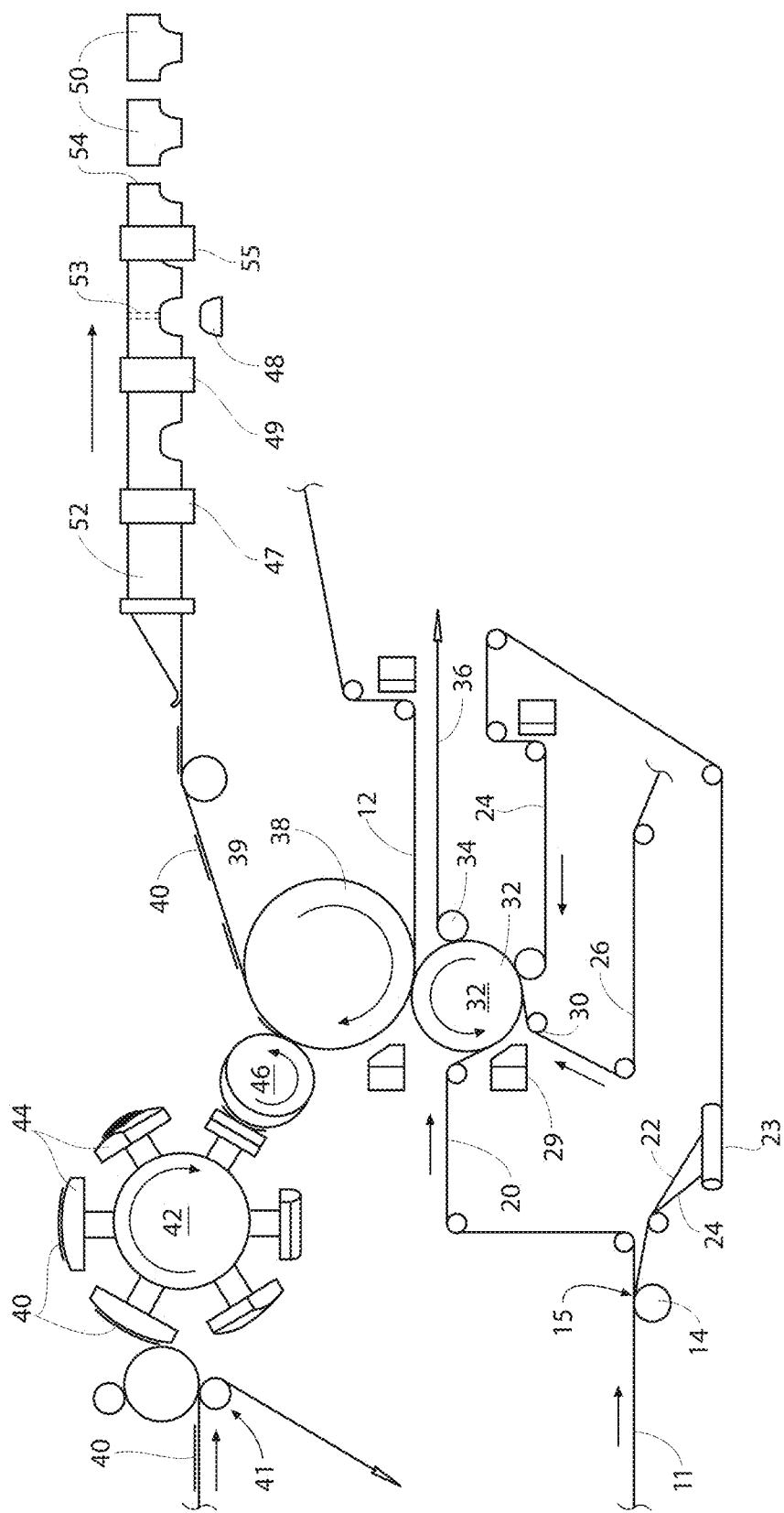
FIG. 2 is a diagrammatic view of the equipment and process shown in FIGS. 1a-1c.
Figure 3A:
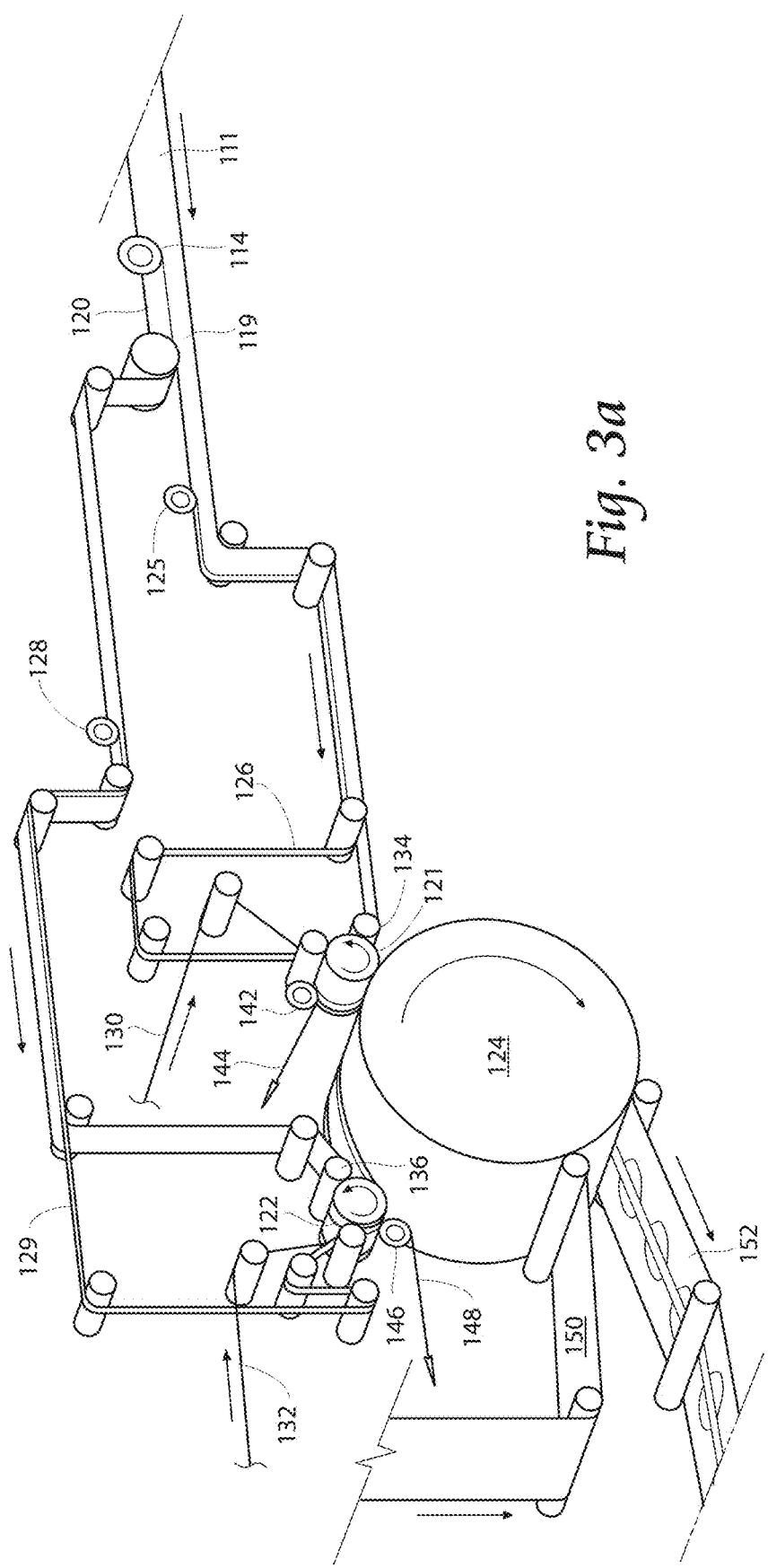
FIGS. 3a-3b are, collectively, a perspective view showing in somewhat diagrammatic fashion an alternative embodiment of the invention.
Figure 3B:
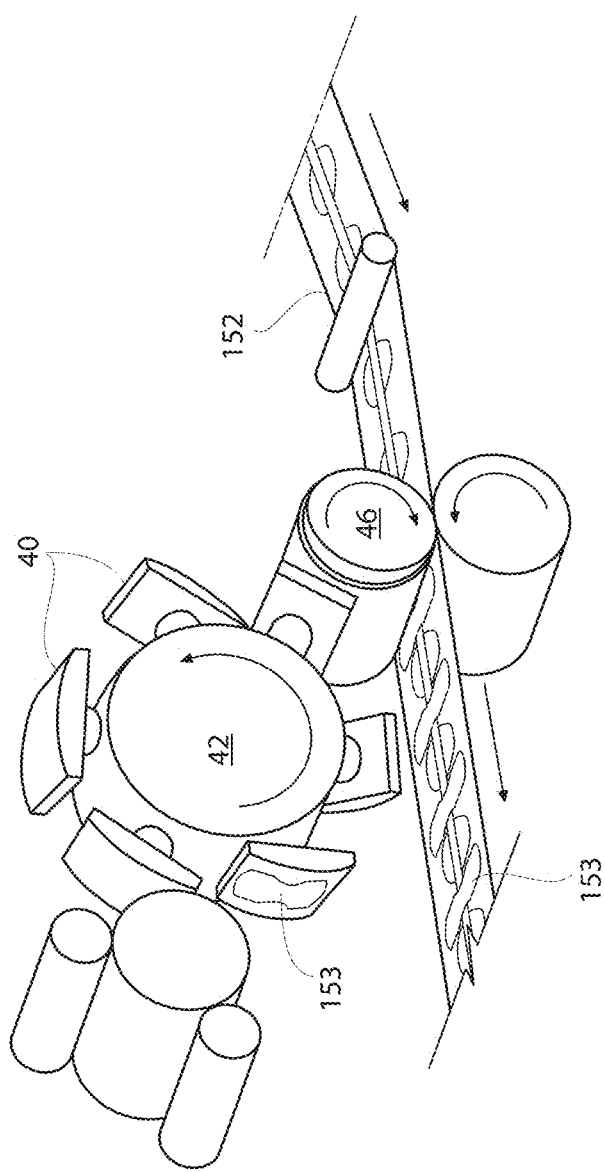
Figure 4:
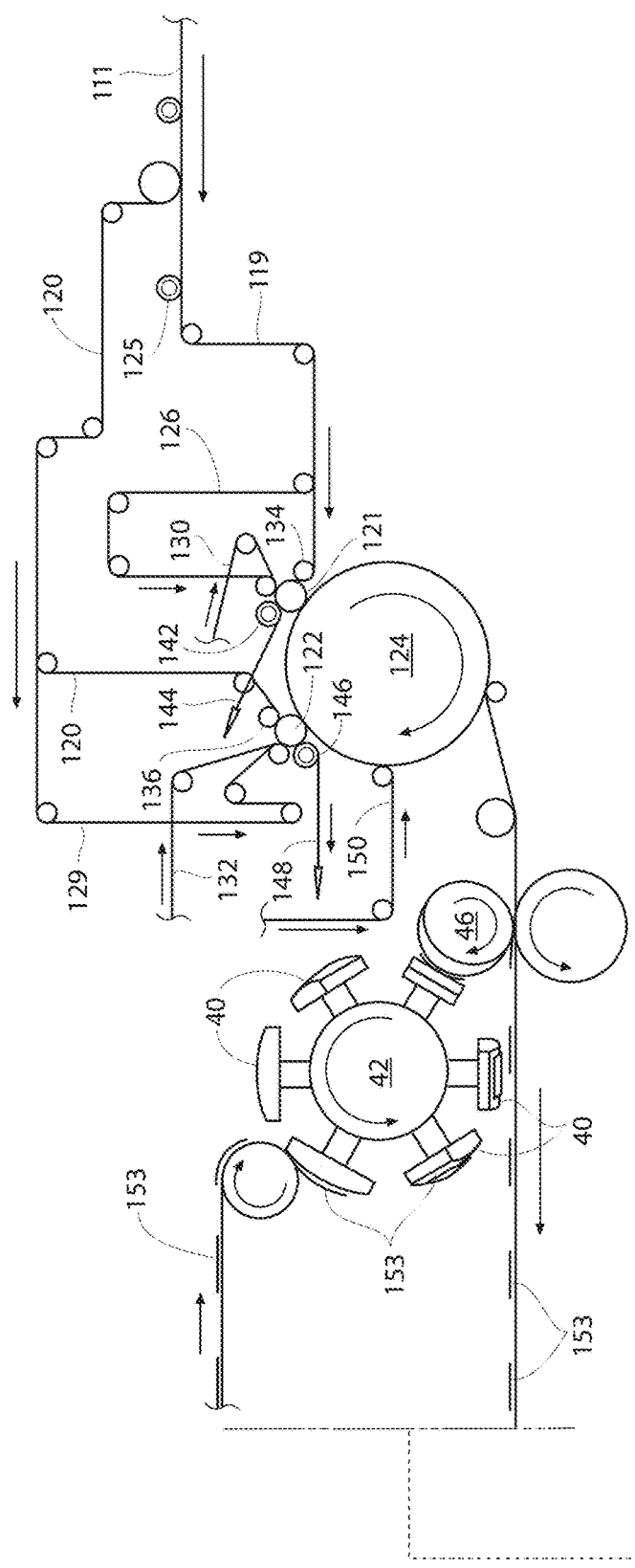
FIG. 4 is a diagrammatic view further illustrating the process and equipment shown in FIGS. 3a-3b.
Figure 4:
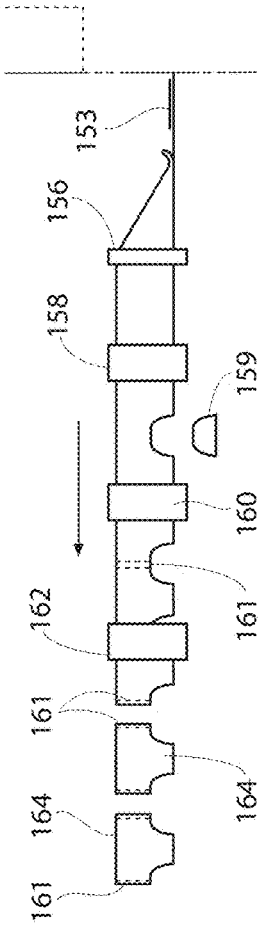

Referring first to FIG. 1a, 1b and 1c, one of the preferred embodiments of the process of this invention and related apparatus are illustrated. The process utilizes two main carrier webs; a non-woven web 11 which forms an inner liner web, while web 12 forms an outwardly facing layer in the finished diaper. In this embodiment, non-woven web 11 is slit, at slitter station 15, by rotary knives 14 along three lines. One of these, line 16, is on approximately the centerline of web 11 and two additional lines 17 and 18 are parallel to and spaced a short distance from centerline 16. The effect is twofold, first, to separate web 11 into two halves, as also seen in FIG. 5b. One half, 19, will become the inside of the front of the diaper 50 and the second half, 20, will become the inside of the back of that garment. Second, two separate, relatively narrow strips 22 and 24 are formed which are subsequently used to cover and entrap portions of the leg-hole elastics 25 and 26. Strips 22 and 24 are separated physically by an angularly disposed spreader roll 23 and aligned laterally with their downstream target positions on the inner edges of webs 19 and 20.

This invention relates particularly to a variation in the way that leg elastics 25 and 26 (which can be ribbons) are applied. In particular, the infeed rate of leg elastics or ribbons 25 and 26 is sped up at the outer extremities of the sine curve in the machine direction so that the vertical component of the velocity of the ribbon placement is at or near the velocity of the substrate web 20 to which the ribbon is applied. This results in little to no tension upon the elastics or ribbons 25 and 26.

Adhesive patterns are applied to the liner webs 20 in target areas for the leg-hole elastics 26. A spray gun assembly 29 of a type known in the art is preferably used to apply the adhesive patterns. Two sets of leg-hole, elastic strands 26 are introduced through laydown guides 30, which reciprocate from side to side past each other. The strands 26 are glued to the web sections 20, their laydown patterns following a serpentine or sinusoidal path. Laydown guides 30 then apply the strands 26, which form leg-hole elastics as the web sections 20 are carried along the face of a drum or roll 32.

In a preferred embodiment of the present invention, the elastics 25 and 26 are laid down in a smooth repetitive oscillation, with a centerline along an line in the machine, and an amplitude in the cross-machine direction. In a preferred embodiment, the infeed velocity of the elastics is increased as the waveform reaches maximum amplitude, then decreases again until the laydown passes the centerline, increasing again until minimum amplitude. This variation decreases neckdown.

Elastic laydown guides 28 and 30 are provided with the ability to make side-to side excursions, and the infeed of elastic 25 and 26 is provided with the ability of variable infeed speed. Elastic laydown guides 28 and 30 can be provided with the ability to make side-to side excursions by an arm that generally travels side to side e.g., by a swinging motion, or slides side to side. The side-to-side excursions of the leg-hole elastic laydown guides 28 and 30 result in generally arcuate segments of elastic strands extending on each side of the web centerline. After the nonwoven strips 22 and 24 have been applied to cover and entrap those parts of the elastics 26 that run nearest to and parallel to the inner edges of the webs 20, a second pair of slitter knives 34 is used to trim away a portion of the narrow nonwoven strips 22, 24, along with that part of the inner liner webs 20 to which they are laminated. This also removes those portions of the elastic strands 26 which are contained within the laminations. The resultant trimmed scrap strips 36 are removed from the process for disposal elsewhere.

The effect of the last-described step is to remove the cut away portions of the elastic, eliminating its corresponding unwanted gathering effect from the crotch region of the garments 50. The remaining portions of the curved elastic strands create a gathering effect around the leg openings of the finished garments 50.

Subsequent to the combining and trimming of the inner webs 20 and the cover strips 22, 24, the combining drum 32 carries the webs to a nip with a second combining drum 38, where the web sections 20, with their respective curved elastic patterns exposed, are transferred to and laminated adhesively against the inside face of outer liner web 12. This process entraps the curved elastic patterns 26 between the inner liners 20 and outer web 12 thereby forming a composite web 39.

The composite web 39 is then provided with a pattern of adhesive in preparation to receive an absorbent insert or patch 46. The patch 46 is cut from a provided patch web 40 by a cooperation of a cutter 41 and an anvil surface on a vacuum roll 42 and rotated into position for transfer to the composite web 39 by a patch applicator 105. If the patch 46 is to be applied to the web 39, a determination explained more fully below, the patch applicator 105 forces the web 39 against the patch 46, thereby adhering the patch 46 to the web 39.

Leg-hole materials 48, if not previously removed, are cut at a cutting station 47, thereby removing the material 48 contained within an approximate perimeter defined by the curved pattern of the elastics 26 and defining one half of a leg opening (with the other half of a leg opening provided in an adjacent leg-hole opening). The running composite chassis web 39 is folded, before or after cutting out of the leg holes, longitudinally along its centerline, thereby generally aligning its front waist edge with its back waist edge. The regions 53 which are to become the side seams 54 of the garments 50 are then welded by a sealing device 49 either ultrasonically or by heat. Note that the leg holes are preferably cut out before this point, leaving only a narrow zone for welding. The weld pattern is preferably wide enough to extend into both the left side seam of one garment and the right side seam of the adjacent garment. The garments 50 are then separated by passing through a cut-off knife assembly 55, which severs the web along the transverse axis of the side seam weld 53.

Figure 5:
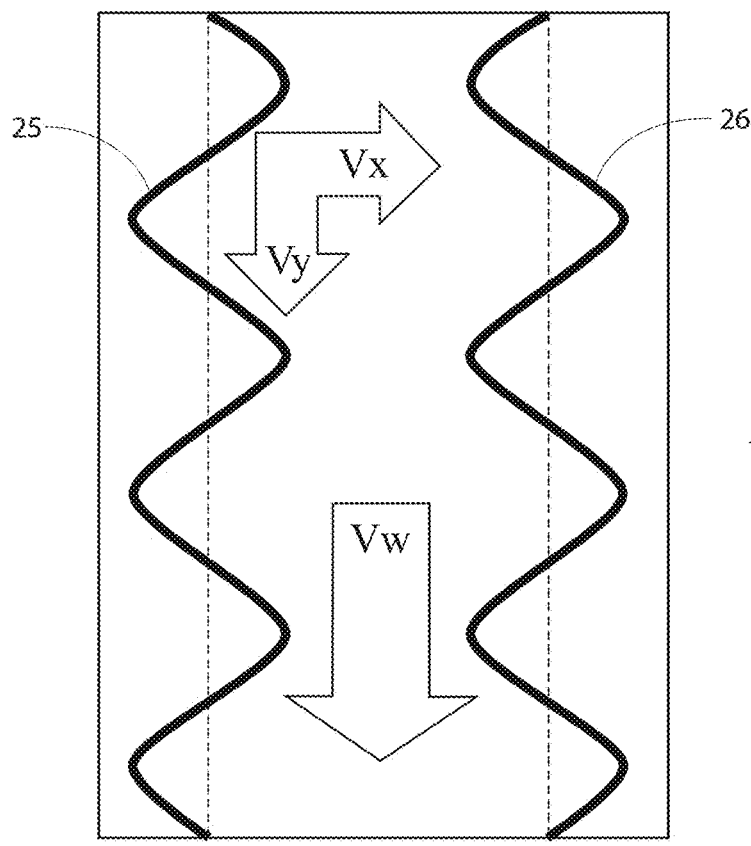
FIG. 5 is a top plan view of a ribbon application sequence of the present invention.

As described above, the laydown guides 30 used to apply the leg-hole elastics 26 to the liner web 20 oscillate from side to side to apply the leg-hole elastic 26 to the liner web 20 in a generally wave-like pattern. It should be understood that due to the oscillating motion of the laydown guides 28 and 30, it is desirable to change the rate at which the leg-hole elastic 25 and 26 is introduced to the liner web 20. As shown in FIG. 5, the velocity of the leg-hole elastic 26 has both a vertical (machine direction) component Vy and a horizontal (cross-machine direction) component Vx. It is contemplated that the vertical component of the velocity of the leg-hole elastic 25 and 26 is equal to, and in the same direction as, the velocity of the liner web 20 on which the leg-hole elastic 26 is being applied.

The incoming ribbon has variable speed, with the incoming ribbon increasing in velocity as the incoming ribbon is deposited in the curved pattern from the centerline to the maximum amplitude (its greatest distance from the centerline in the cross-machine direction towards a first boundary of the web), decreasing as the incoming ribbon is deposited in the curved pattern from the maximum amplitude to the centerline, and increasing as the incoming ribbon is deposited in the curved pattern from the centerline to the minimum amplitude (its greatest distance from the centerline in the cross-machine direction towards the other boundary of the web).

In a preferred elastic laydown pattern such as shown in FIG. 5, two lanes of elastic 25 and 26 are laid down in separate lanes, with both minimum amplitudes in the same position in the machine direction.

At least one web accumulator (not shown) can be located upstream of, or before, the leg-hole elastic guides 30, as shown in FIG. 1a. The accumulator can take any form, such as a servo driven roller that speeds up and slows down, an alternate roller configuration, a rocking roller configuration, or any different means of accumulating the web, such as a miniature accumulator, or a device similar to a diaper cross-folder, or a tucker blade.

In this manner, the rate at which the leg-hole elastics 26 are being fed to the liner web 20 can be altered while the rate at which the leg-hole elastics 26 is fed to a rate adjustment apparatus 314 (not shown) remains the same.

It is further contemplated that the system may include a tension control device (not shown). The tension control device is preferably sized and configured to eliminate tension in the leg-hole elastic 26 prior to applying the leg-hole elastic 26 to the liner web 20. In this manner when the leg-hole elastic 26 is applied to the liner web 20, the leg-hole elastic will not become misshapen as it would if the leg-hole elastic 26 were under tension. The tension control device can takes the form of a web accumulator, or any form known in the art capable of performing such a function.

In this manner, the leg-hole elastic 26 is accumulated in the tension control device when the rate of application of the leg-hole elastics 26 to the liner web 20 is slowed as described above. It is contemplated that the above-described system will provide active tension control and feed approach to change the feed of the leg-hole elastics 26 to the liner web 20 so that the leg-hole elastic is not under tension when it is applied to the liner web 20. This will result in leg-hole elastics 26 that are applied to the liner web 20 in an undistorted manner.

Figure 6:
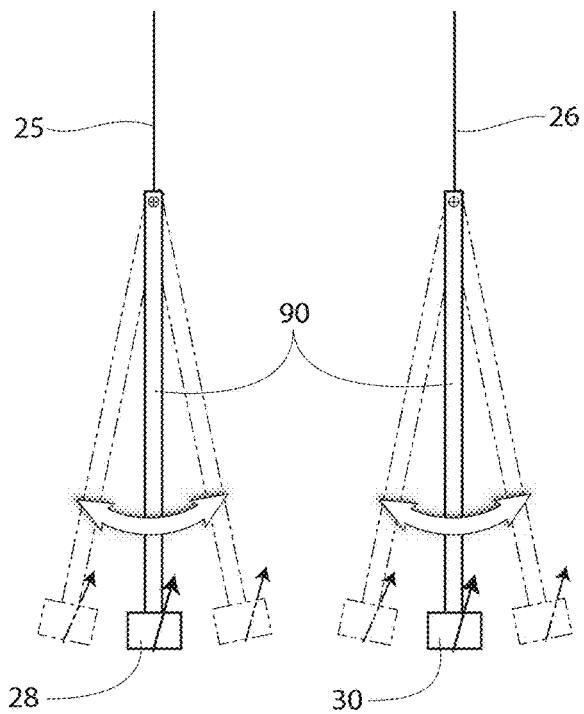
FIG. 6 is a top view of an exemplary pair of swinging arms for applying elastic in a wave (or other) pattern on a running web.

Referring now to FIG. 6, a top view of an exemplary pair of swinging arms 90 for applying elastics 25 and 26 is shown. The swinging arms can be programmed or operated to apply the elastics in a wave pattern (see, e.g., FIG. 5) on a running web such as shown in FIG. 1.

It should be understood that the above-described arrangement may be used to apply any type of material to a moving web in a curved pattern. In the illustrated example, the material is leg-hole elastics 26 taking the form of elastic strands; however it is contemplated that the material could take the form of elastic tape. It is further contemplated that the material could take the form of non-elastic strands or non-elastic tape.

Figure 7:
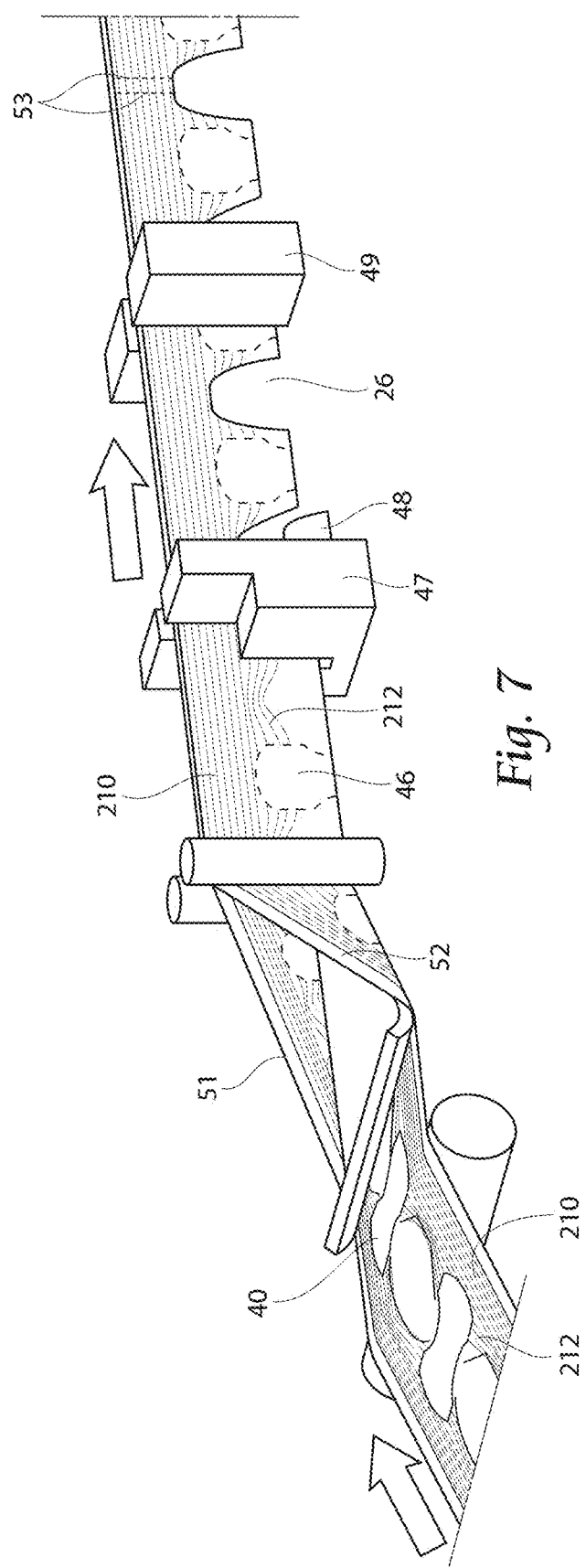
FIG. 7 is a perspective view showing a preferred embodiment of the invention in somewhat diagrammatic fashion, used to create a pant-type diaper with waist band elastics and parallel flared elastics, with a portion of the curved elastics removed by a chip in a leg opening section of the pant-type diaper.

Referring now to FIG. 7, a perspective view showing a preferred embodiment of an alternative embodiment of the present invention is shown. This embodiment is used to create a pant-type diaper with waist band elastics and curved elastics, with a portion of the curved elastics removed by a chip in a leg opening section of the pant-type diaper.

In this embodiment, two or more series of leg band elastics 210 and 212 are laid down. Preferably waistband elastics 210 run parallel to one another, while another sequence of leg and waist elastics 212 are laid down in a curved pattern inboard of the waistband elastics 210. Preferably, the leg and waist elastics 212 are applied in a curved fashion. At what will become the leg hole opening of the diaper, the leg and waist elastics 212 are generally parallel, and each of the independent the leg and waist elastics 212 are then curved towards absorbent insert or patch 46, and increasingly separated in distance from one another the closer the leg and waist elastics 212 get to the absorbent insert or patch 46.

As described above, sliding laydown guides 30 can be used to apply the leg and waist elastics 212 to the liner web 20, the laydown guides oscillates from side to side to apply the leg and waist elastics 212 to the liner web 20 in a generally wave-like pattern. Alternatively, a swing arm or series of swing arms 90 such as shown in FIG. 6 can be used to apply the leg and waist elastics 212. The swing arms 28 and 30, or the sliding layding guides 30 can be programmed to move in a predetermined fashion in order to lay down a straight line of elastics 26 in a machine direction by remaining in a constant position, or can lay down a patterned shape of elastics 26 by moving from side to side as desired.

Figure 8:
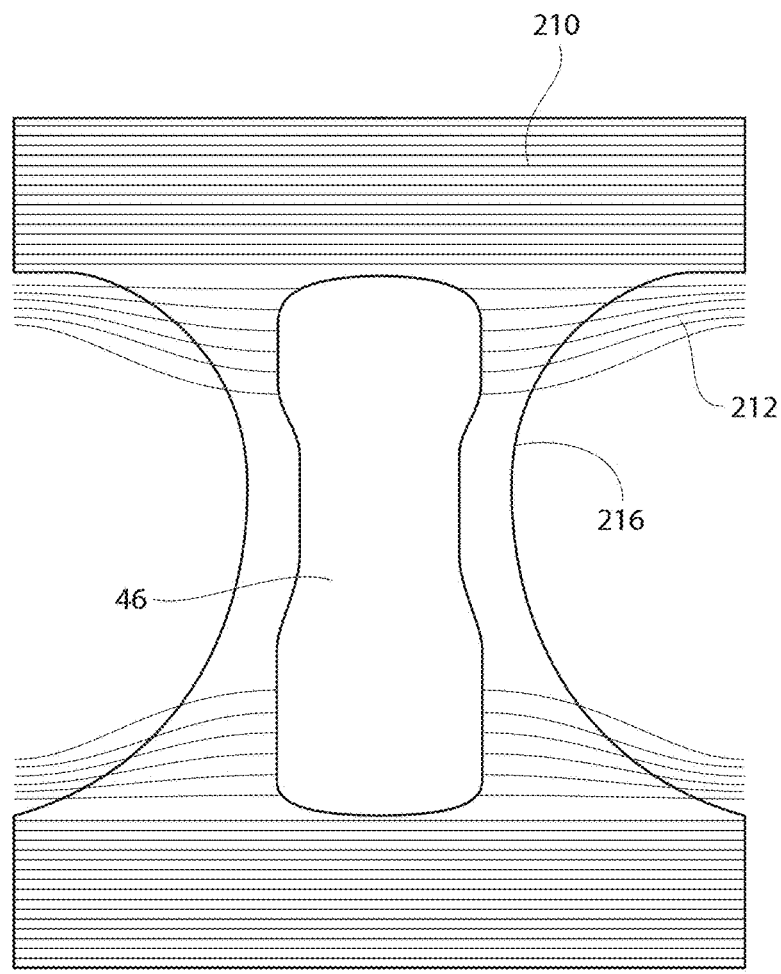
FIG. 8 is a plan view of a pant-type diaper with waist band elastics and curved elastics, with a portion of the curved elastics removed by a chip in a leg opening section of the pant-type diaper prior to bonding a front portion of the diaper with a rear (or back) portion of the diaper.
Figure 9:
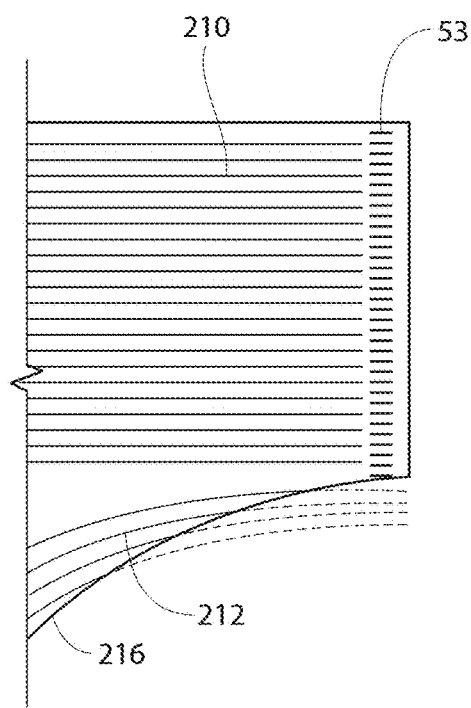
FIG. 9 is a plan view of a portion of a pant-type diaper showing a side seam bond between and front and a rear portion of the diaper, showing parallel flared elastics extending to a die cut leg cutout area, where the parallel flared elastics are removed.

Referring now to FIGS. 8 and 9, plan views of a pant-type diaper with parallel waist band elastics 210 and flared leg and waist elastics 212 is shown.

Similar to the configuration shown in FIG. 1b, leg-hole materials 48, if not previously removed, are cut at a cutting station 47 (FIG. 7), thereby removing the material 48 and forming a leg opening contour 216 on both the left and the right sides of the product. Referring particularly to FIG. 9, it can be seen that the leg and waist elastics 212 do not occupy what later will become seam 53, but instead pass through leg opening contours 216 for removal at cutting station 47 (FIG. 7).

Figure 10:
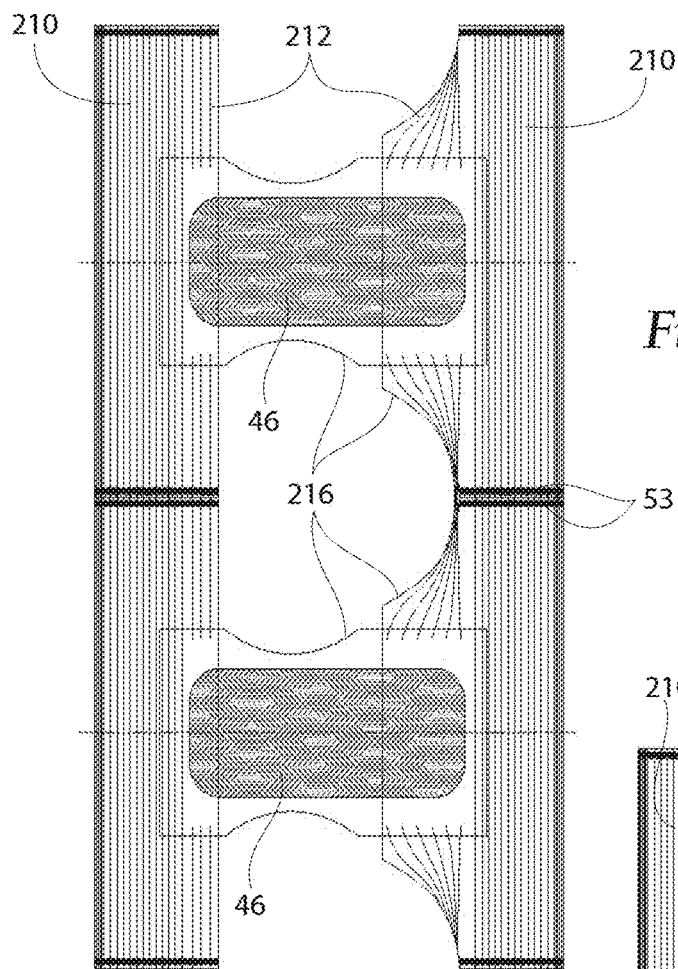
FIGS. 10-12 are in-process top views of pant type diapers with varying applications of straight and curved elastics.
Figure 11:
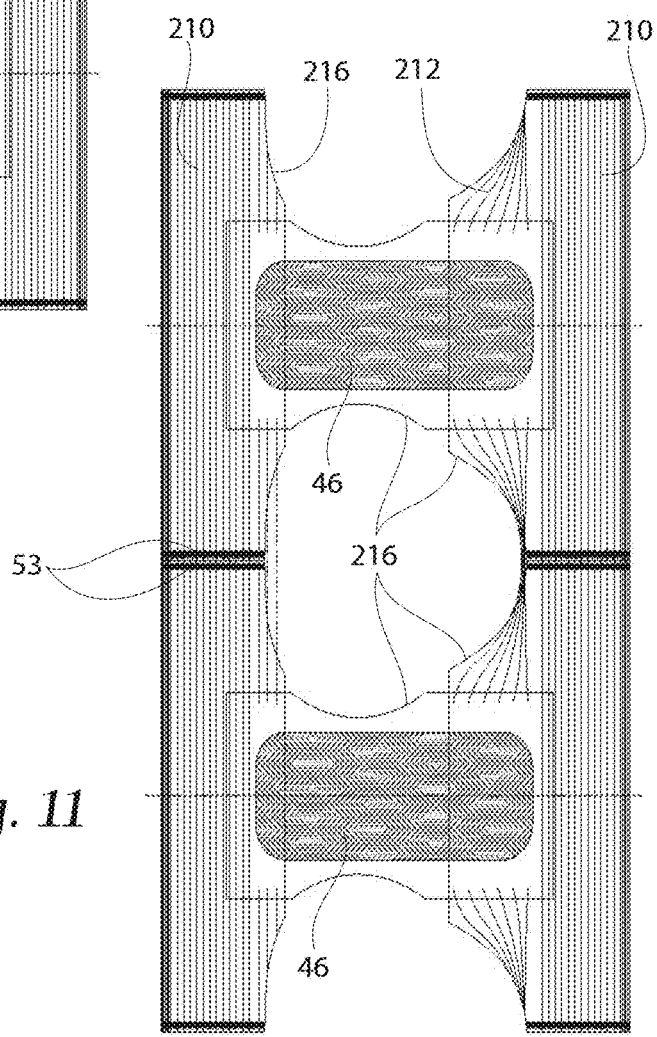
Figure 12:
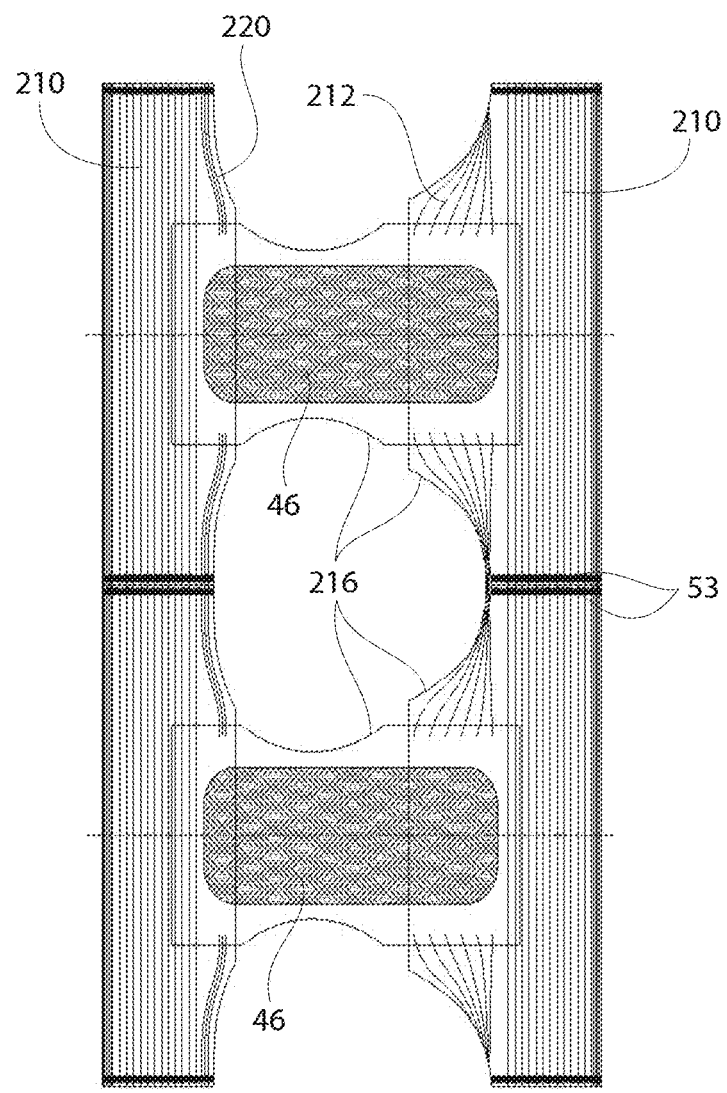

Referring now to FIGS. 10-12, these figures show in-process top views of pant type diapers with varying applications of straight and curved elastics.

As shown in FIG. 10, in one embodiment, parallel waist elastics 210 are applied to both the front and the back, and a series of parallel leg and waist elastics 212 are provided on a front of the product, while curved leg and waist elastics 212 are provided on the rear of the product. The curved leg and waist elastics 212 of the rear of the product would cross a secondary leg contour 216 of the product, and those elastics would not be contained within the side seam bond 53.

Referring to FIG. 11, parallel waist elastics 210 are applied to both the front and the back, and a series of parallel leg and waist elastics 212 are provided on a front of the product, while curved leg and waist elastics 212 are provided on the rear of the product. The curved leg and waist elastics 212 of the rear of the product would cross a secondary leg contour 216 of the product, and those elastics would not be contained within the side seam bond 53. Similarly, a portion of the parallel leg and waist elastics 212 of the front of the product would enter a tertiary leg contour 216, and some of those parallel leg and waist elastics 212 would be severed during chip removal.

In the embodiment shown in FIG. 12, curved leg and waist elastics 220 are provided on the front of the product, and curved leg and waist elastics 212 which do not enter the side seams 53 are provided on the rear of the product. These and other elastic lay down variations, including following the leg cut in a tight group, a combination of a flared feature on the back (or front); and the opposing sides with elastics are tightly grouped together following a leg cut die and going through the leg cut die; or no elastics in those portions, are all contemplated.

Referring now to FIGS. 13-16 generally, a series of elastic break brakes 300 are provided throughout a travel path of elastics (such as elastic 26) in a machine operation. Elastic strands thread through each individual brake mechanism 300, and if an elastic strand breaks downstream, a natural snap back of the elastic, which ordinarily travels through the system under tension, drives an immediately upstream cam mechanism back, and holds the elastic thread in place at the elastic break brake 300 immediately upstream of the break as to minimize rethreading required downstream of the elastic break brake.

Referring generally to FIGS. 13-17, an elastic break brake 300 to allow downstream travel of an elastic thread during machine operation and to stop unwanted elastic travel is disclosed. A rotating weight 310 is carried by a pin 308 coupled to a base 306. A base elastic retaining surface 312 spaced apart from said rotating cam weight 310. The rotating cam weight 310 is rotatable by the force of elastic 26 traveling under tension between said rotating cam weight 310 and said base elastic retaining surface 312. The force of the traveling elastic 26 causes the cam weight 310 to be slightly rotated in a downstream machine direction allowing passage of said elastic 26 during machine operation. If a break in the elastic 26 occurs, the elastic goes limp and therefore the force of the traveling elastic 26 is no longer enough to hold the rotating cam weight 310 in its slightly downstream rotated position. Instead, the cam weight 310 rotates back upstream due to gravity and the absence of the force from elastic 26 traveling under tension. The elastic 26 is then trapped between the cam weight 310 and the elastic retaining surface 312. This prevents unwanted elastic 26 travel, and makes the task of re-threading the elastic 26 far shorter.

Figures 13, 14:
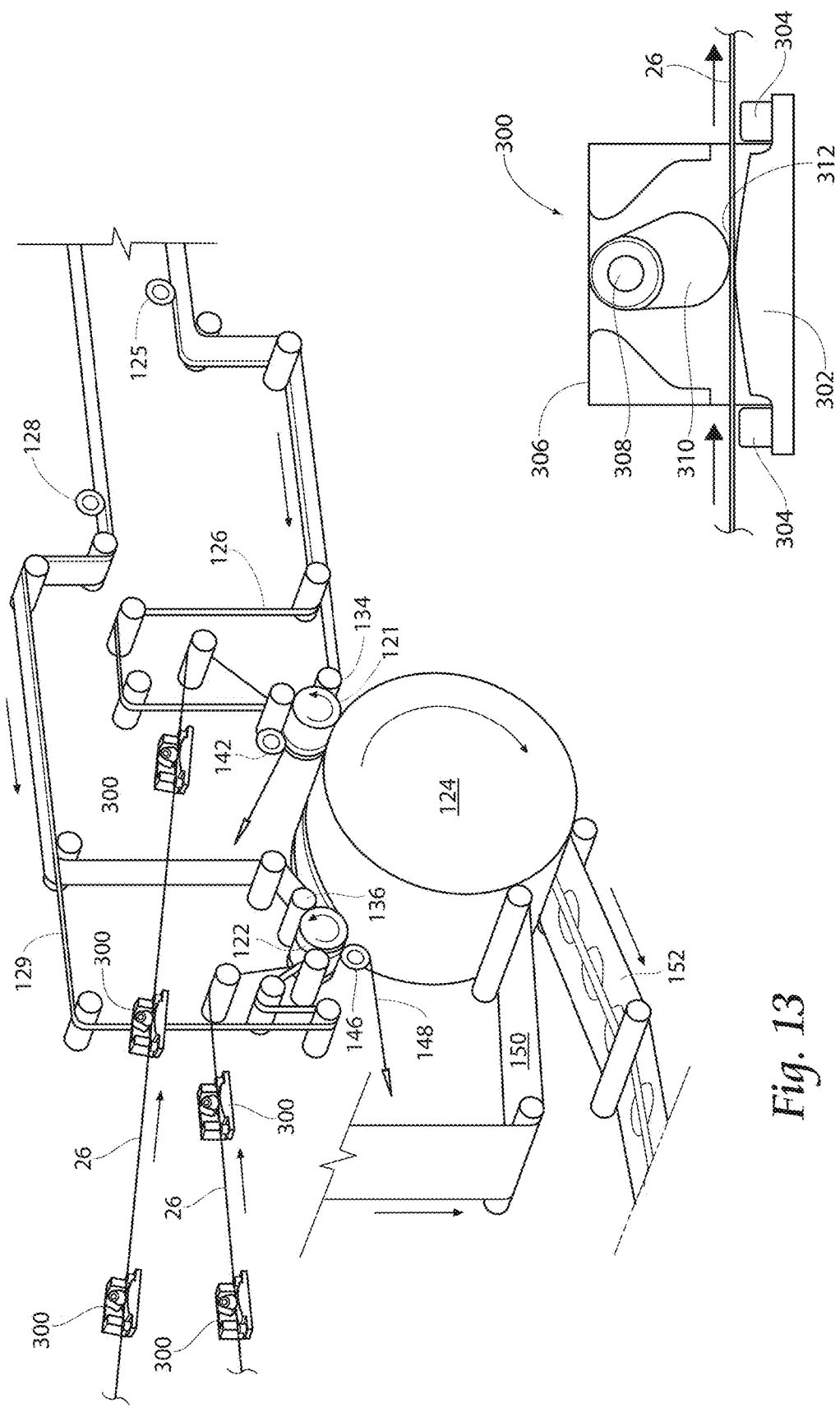
FIG. 13 is a perspective view showing in somewhat diagrammatic fashion an application of the elastic break brake invention, with a series of elastic break brakes applied throughout the travel path of introduced elastic webs.
FIG. 14 is a side view of elastic break brakes of the present invention, carrying an elastic strand between a rotating cam and a base.

Referring now to FIG. 13, a perspective view of a representative elastic travel sequence is shown in somewhat diagrammatic fashion. A series of elastic break brakes 300 are provided throughout the travel path of introduced elastic webs, and through each elastic break brake 300, the continuous web of elastic is threaded.

Referring to FIG. 14, a side view of elastic break brakes 300 of the present invention are shown carrying an elastic strand 26. A securing mechanism(s) 304 holds the elastic break brakes 300 in place. The elastic is threaded between a rotating cam weight 310 and a base elastic retaining surface 312, which is very closely spaced apart from the rotating cam weight 310. The rotating cam weight 310 is carried by pin 308 coupled to a base back 306 generally depending from base 302.

During routine operation, the elastic 26 is traveling under tension, and at speed, sufficient to cause the cam weight 310 to be slightly rotated in the downstream (machine) direction. Elastic 26 is allowed to and capable of passing between the cam weight 310 and the base elastic retaining surface 312.

Figure 15:
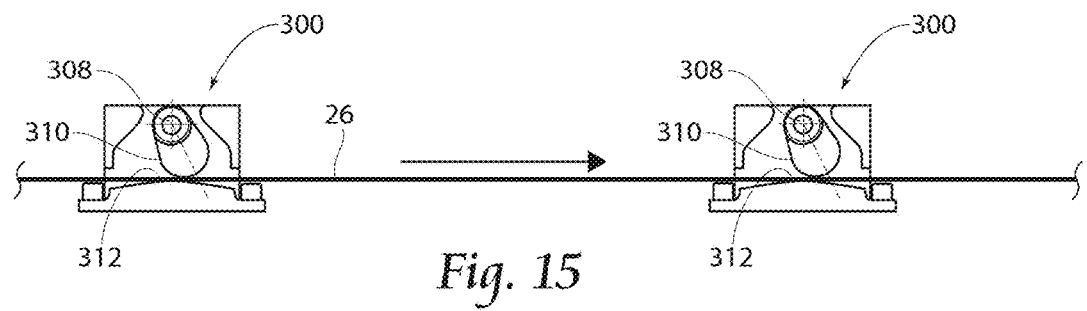
FIG. 15 is a side view of a series of elastic break brakes of the present invention, carrying an elastic strand.

Referring now to FIG. 15, should a break in the elastic strand 26 occur upstream of a series of the elastic break brakes 300, the elastic break brake immediately upstream of the break in the elastic would, due to gravity or otherwise (e.g., a spring mechanism, or motor controlled) rotate counterclockwise to cinch the elastic strand 26 between the cam weight 310 and the base elastic retaining surface 312. By maintaining control of the elastic 26 just upstream of the break point of the elastic 26, only re-threading downstream of the activated elastic break brake 300 is required.

Figure 16:
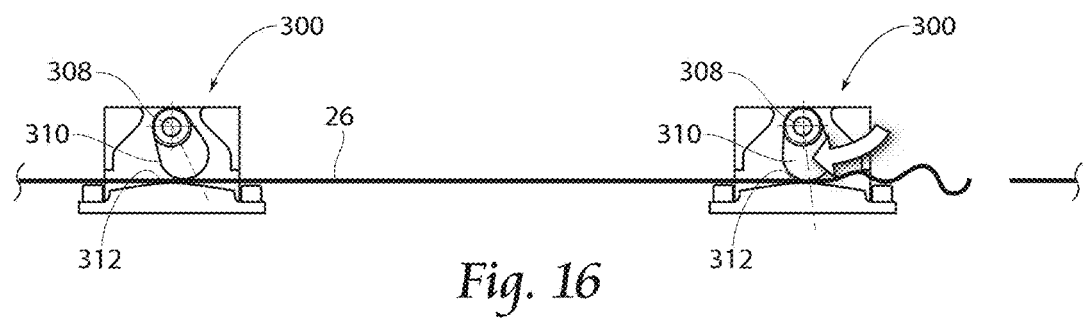
FIG. 16 is a side view of elastic break brakes of the present invention, carrying an elastic strand between a rotating cam and a base, with a break in the elastic strand upstream of a series of the elastic break brakes, the elastic break brake immediately upstream of the break rotating counterclockwise to cinch the elastic strand between the rotating cam and the base and holding the elastic strand such that only re-threading downstream of this elastic break brake is required.
Figure 17:
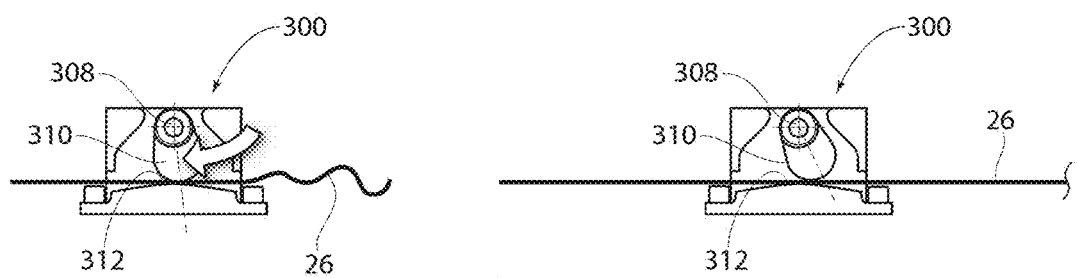
FIG. 17 is a side view similar to FIG. 16, with a break in the elastic strand between two elastic break brakes, the elastic break brake immediately upstream of the break rotating counterclockwise to cinch the elastic strand between the rotating cam and the base and holding the elastic strand such that only re-threading downstream of the first elastic break brake is required.

Similarly, as shown in FIG. 16, should a break in the elastic strand 26 occur between two elastic break brakes 300, the elastic break brake 300 immediately upstream of the break would due to gravity or otherwise (e.g., controlled) rotate counterclockwise to cinch the elastic strand 26 between the cam weight 310 and the base elastic retaining surface 312. By maintaining control of the elastic 26 just upstream of the break point of the elastic 26, only re-threading downstream (in the machine direction) of the activated elastic break brake 300 would be required.

Referring now to FIGS. 18-23, top views of pant type diapers with varying applications of straight and curved elastics are shown.

Figure 18:
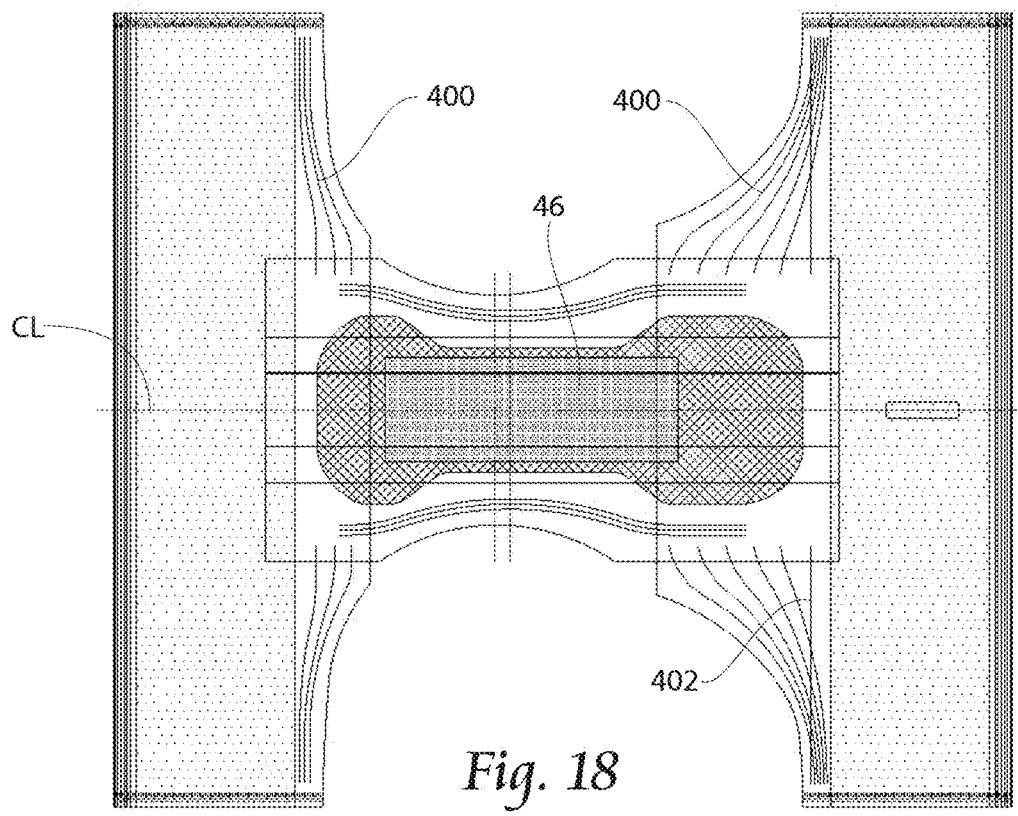
FIGS. 18-23 are top views of pant type diapers with varying applications of straight and parallel flared elastics.

Referring to FIG. 18, a series of flared elastics 400 are provided on a front and a back of a pant type diaper. On the back side, a single straight elastic strand 402 is provided, which is crossed over by the flaring elastics 400 of the back side of the pant.

Figure 19:
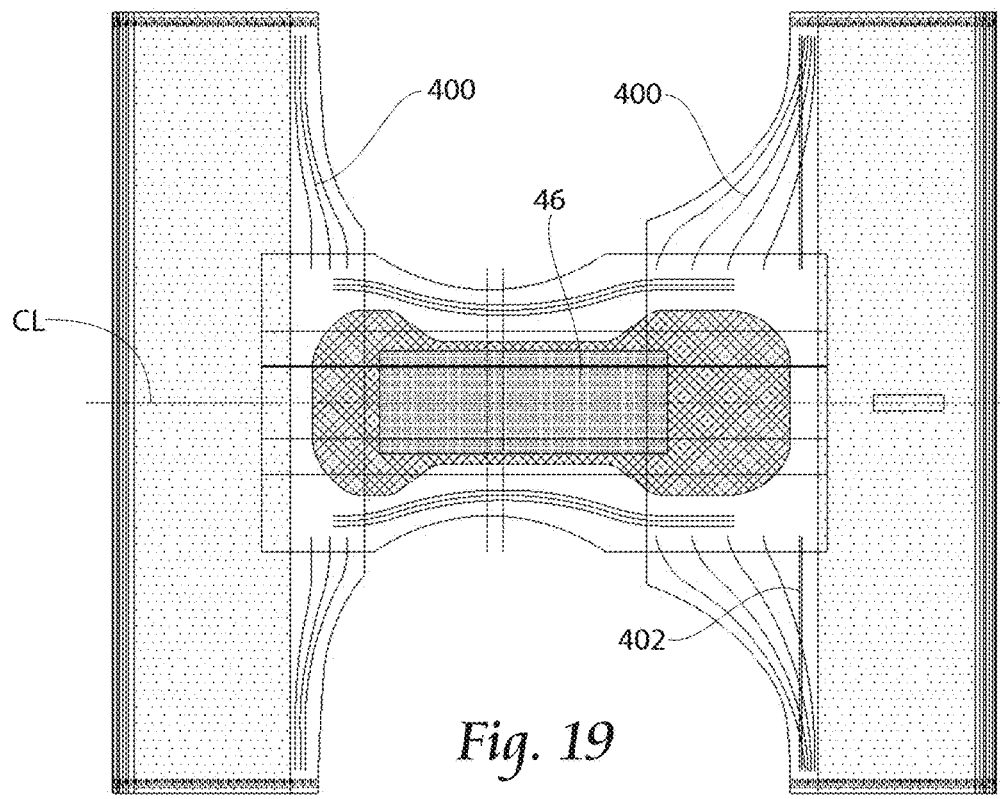

In FIG. 19, multiple straight elastic strands 402 are provided on the rear of the diaper, which are crossed over by the flaring elastics 400.

Figure 20:
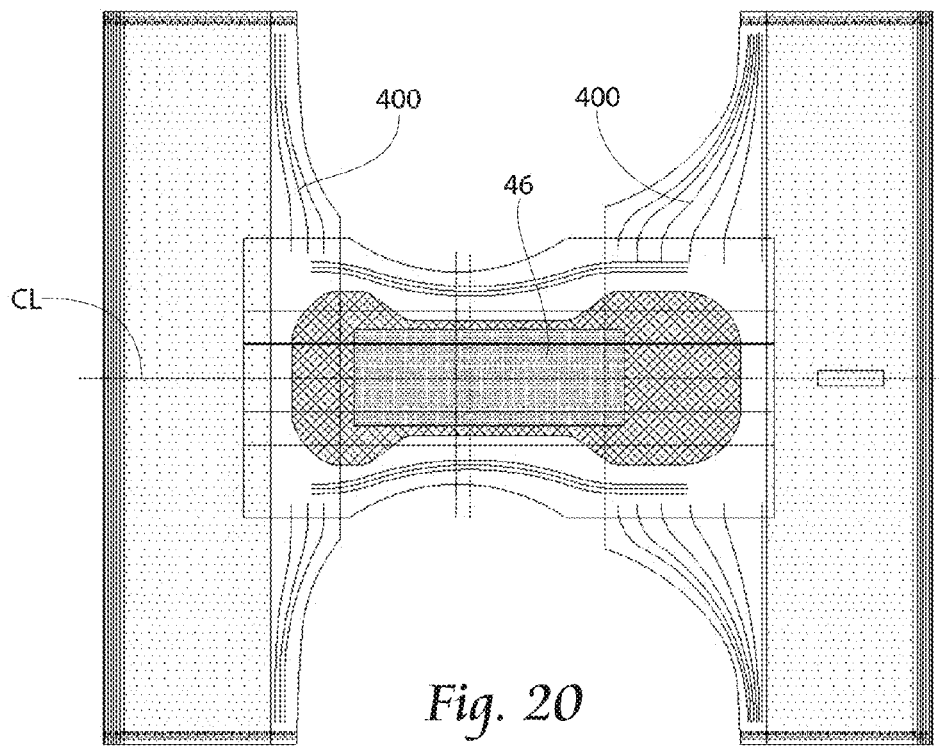
Figure 21:
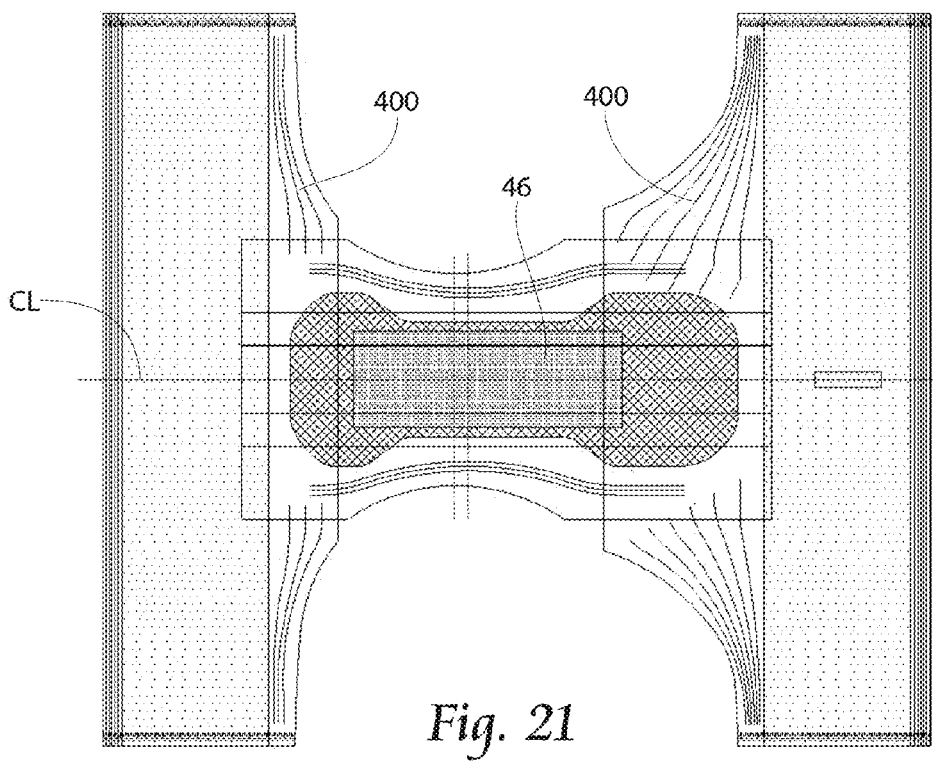

Referring to FIG. 20, another novel elastic laydown pattern is shown. In this embodiment, the distance between successive strands of the flared elastics 400 on the rear side decreases towards the center of the diaper. A similar embodiment is shown in FIG. 21, but the flaring elastics 400 on the rear stop well short of a centerline CL of the product and are discontinued across the crotch portion of the product.

Figure 22:
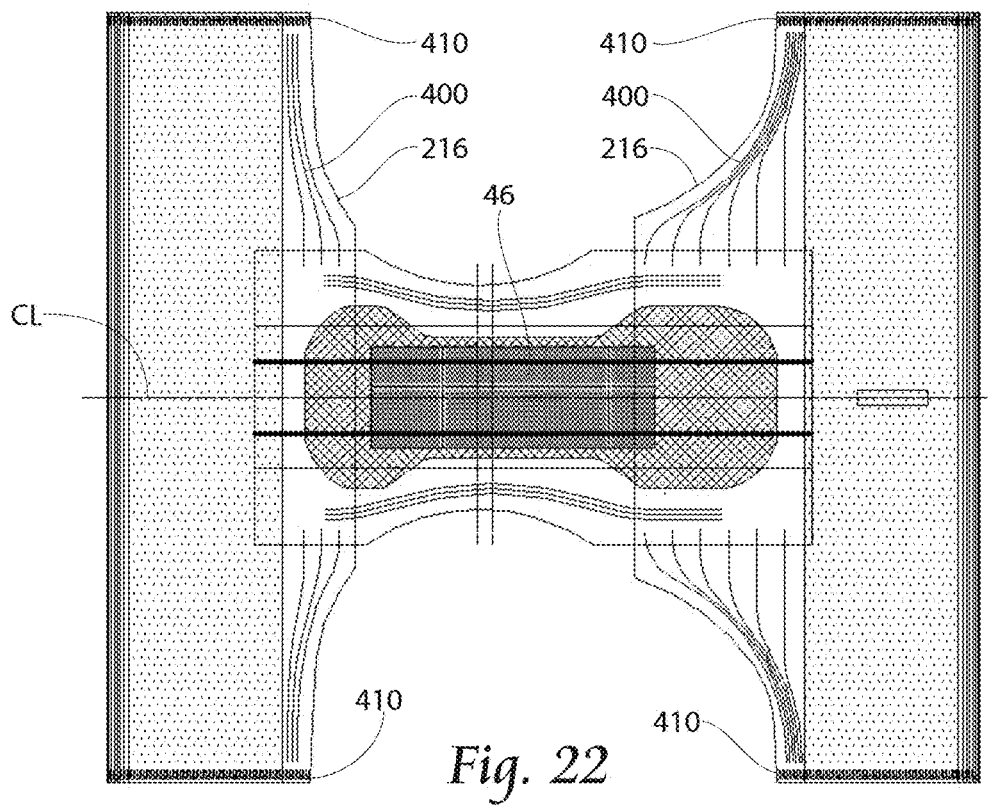
Figure 23:
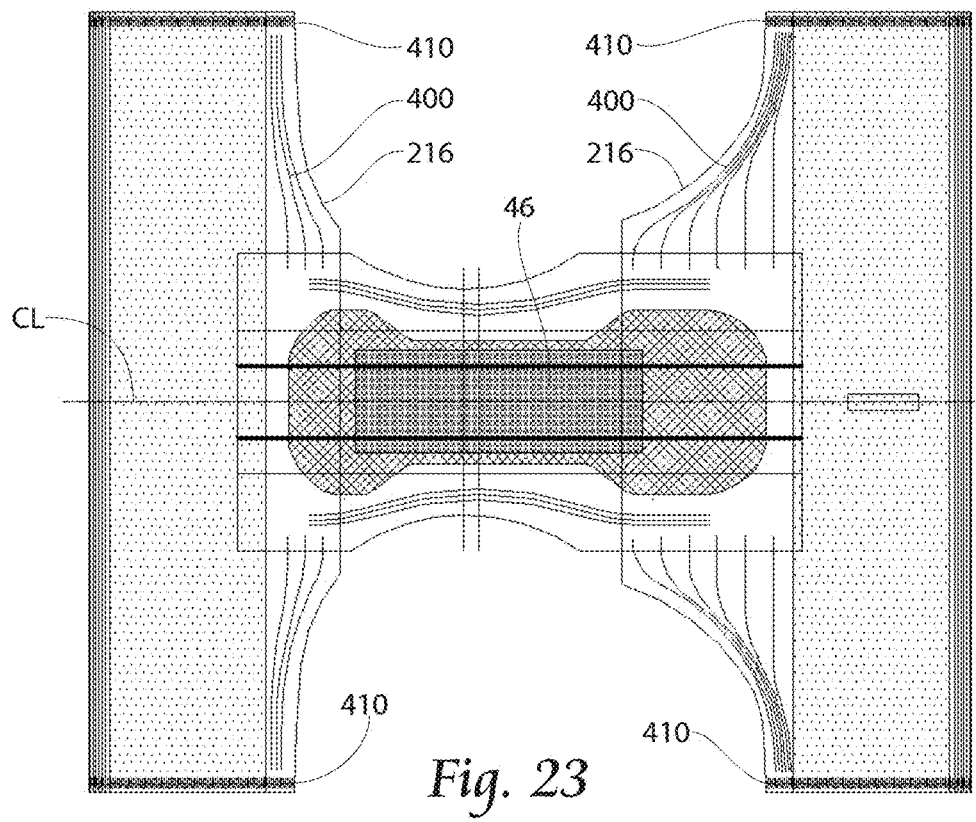

Referring to FIGS. 22 and 23, the elastics 400 do not fan, but instead are parallel to one another generally along a leg cutout 216, and then run parallel to each other through the centerline CL of the product. This configuration is a flared configuration. In this arrangement, the elastics 400 run from near the disposable product side areas 410 (when worn about the waist of a user) and run parallel from there, toward the crotch portion of the diaper, and particularly toward the absorbent core 46 crossing the centerline CL. In this sense, the elastics 400 generally are running in a direction that is skew to the machine direction. Each of the elastics 400 eventually turns to the centerline CL and next runs in the machine direction for a segment. At the centerline. Throughout the elastic laydown sequence, elastics 400 will be parallel, but spaced apart based on the time the elastic departs from the generally parallel to the leg cutout 216 direction, to the machine direction. At the parallel to the leg cutout 216 direction, the plurality of elastic strands 400 are considered running in parallel skew to the machine direction, that is neither in the machine direction or the cross machine direction. Still running in parallel, the elastic 400 pattern is mirrored, and the elastics return the flare to a second side area 410 of the product, resulting in a parallel flared elastic pattern. Additionally, at least one of the front or back set of elastics 400 could run entirely curved and parallel along their traverse of the front or back panel.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. An elastic break brake to allow downstream travel of an elastic thread during machine operation and to stop unwanted elastic travel, said elastic break brake comprising:
   a base, a base back depending from said base, a pin coupled to said base back said pin having an axis of rotation, and a rotating cam weight carried by said pin and rotatable coaxially with said axis of rotation;
   a base elastic retaining surface spaced apart from said rotating cam weight;
   a nip point between said base elastic retaining surface and said rotating cam weight, said pin vertically aligned with said nip point;
   said rotating cam weight rotatable in downstream machine direction by elastic traveling under tension between said rotating cam weight and said base elastic retaining surface, allowing passage of said elastic during machine operation, and rotatable in an upstream direction if the elastic is broken to cinch the elastic between the rotating cam weight and the base elastic retaining surface thereby stopping said elastic.

* * * * *